US010702328B2

(12) United States Patent
Slatkine et al.

(10) Patent No.: US 10,702,328 B2
(45) Date of Patent: Jul. 7, 2020

(54) DEVICES AND METHODS FOR TISSUE VAPORIZATION

(71) Applicant: Novoxel Ltd., Natania (IL)

(72) Inventors: Michael Slatkine, Herzlia (IL); Raphael Shavit, Tel-Aviv (IL); Jacob Zlochover, Pardes Chana-Karkur (IL)

(73) Assignee: Novoxel Ltd., Natania (IL)

( * ) Notice: Subject to any disclaimer, the term of this patent is extended or adjusted under 35 U.S.C. 154(b) by 276 days.

(21) Appl. No.: 15/105,086

(22) PCT Filed: Dec. 16, 2014

(86) PCT No.: PCT/IL2014/051103
§ 371 (c)(1),
(2) Date: Jun. 16, 2016

(87) PCT Pub. No.: WO2015/092791
PCT Pub. Date: Jun. 25, 2015

(65) Prior Publication Data
US 2016/0317208 A1    Nov. 3, 2016

Related U.S. Application Data

(60) Provisional application No. 61/917,435, filed on Dec. 18, 2013.

(51) Int. Cl.
*A61B 18/04*    (2006.01)
*A61B 18/08*    (2006.01)
(Continued)

(52) U.S. Cl.
CPC ............ *A61B 18/082* (2013.01); *A61B 18/08* (2013.01); *A61B 18/14* (2013.01);
(Continued)

(58) Field of Classification Search
CPC ....... A61B 18/08; A61B 18/082; A61B 18/14; A61B 2018/00148; A61B 2018/0019;
(Continued)

(56) References Cited

U.S. PATENT DOCUMENTS 2,894,512 A    7/1959 Tapper
3,020,912 A    2/1962 Chester
(Continued)

FOREIGN PATENT DOCUMENTS

EP    1563788    8/2005
EP    1726329    11/2006
(Continued)

OTHER PUBLICATIONS

Subramanian, Chinnia & Cavallaro, Giuseppe & Winkelman, Graham. (2000). Wear maps for titanium nitride coatings deposited on copper and brass with electroless nickel interlayers. Wear. 241. 228-233. 10.1016/50043-1648(00)00380-X. (Year: 2000).*
(Continued)

*Primary Examiner* — Jaymi E Della
(74) *Attorney, Agent, or Firm* — Brown Rudnick LLP

(57) ABSTRACT

In accordance with some embodiments of the invention there is provided a device for vaporizing one or more holes in tissue, comprising an array of vaporizing elements and a heating element configured to heat the vaporizing elements, wherein a geometry of at least a portion of the vaporizing elements is configured to prevent excessive penetration of other vaporizing elements into the tissue. In some embodiments, the vaporizing elements are heated to a temperature ranging between 300-600 degrees Celsius.

24 Claims, 26 Drawing Sheets

(51) Int. Cl.
*A61B 18/14* (2006.01)
*A61B 18/00* (2006.01)

(52) U.S. Cl.
CPC .............. *A61B 2018/0013* (2013.01); *A61B 2018/0019* (2013.01); *A61B 2018/00095* (2013.01); *A61B 2018/00142* (2013.01); *A61B 2018/00148* (2013.01); *A61B 2018/00196* (2013.01); *A61B 2018/00452* (2013.01); *A61B 2018/00625* (2013.01); *A61B 2018/00916* (2013.01); *A61B 2018/00994* (2013.01); *A61B 2018/143* (2013.01)

(58) Field of Classification Search
CPC ........... A61B 2018/00196; A61B 2018/00452; A61B 2018/00625; A61B 2018/00916; A61B 2018/00994; A61B 2018/143; A61B 2018/00107; A61B 2018/0016; A61B 2018/1425; A61B 2018/1432
See application file for complete search history.

(56) References Cited

U.S. PATENT DOCUMENTS

| | | | |
|---|---|---|---|
| 3,875,944 | A | 4/1975 | Toyama |
| 4,736,743 | A | 4/1988 | Daikuzono |
| 4,799,478 | A | 1/1989 | Fedorov et al. |
| 5,019,076 | A | 5/1991 | Yamanashi et al. |
| 5,064,426 | A | 11/1991 | Huebsch |
| 5,123,028 | A | 6/1992 | Hobart et al. |
| 5,318,562 | A | 6/1994 | Levy et al. |
| 5,360,447 | A | 11/1994 | Koop |
| 5,411,502 | A | 5/1995 | Zair |
| 5,417,687 | A * | 5/1995 | Nardella ............ A61B 17/3476 604/164.08 |
| 5,423,803 | A | 6/1995 | Tankovich et al. |
| 5,498,258 | A | 3/1996 | Hakky et al. |
| 5,655,547 | A | 8/1997 | Karni |
| 5,733,278 | A | 3/1998 | Slatkine et al. |
| 5,885,211 | A | 3/1999 | Eppstein et al. |
| 5,891,142 | A * | 4/1999 | Eggers ............... A61B 18/1442 606/51 |
| 5,899,915 | A | 5/1999 | Saadat |
| 5,908,419 | A | 6/1999 | Hahnen et al. |
| 6,142,939 | A | 11/2000 | Eppstein et al. |
| 6,296,639 | B1 | 10/2001 | Truckai et al. |
| 6,383,179 | B1 | 5/2002 | Neuberger |
| 6,475,138 | B1 | 11/2002 | Schechter et al. |
| 6,475,547 | B1 | 11/2002 | Lignell et al. |
| 6,530,915 | B1 | 3/2003 | Eppstein et al. |
| 6,678,556 | B1 | 1/2004 | Nolan et al. |
| 7,537,590 | B2 | 5/2009 | Santini et al. |
| 8,690,865 | B2 | 4/2014 | Prausnitz et al. |
| 8,808,311 | B2 | 8/2014 | Heinrich et al. |
| 8,834,461 | B2 | 9/2014 | Werneth et al. |
| 8,876,811 | B2 | 11/2014 | Lewinsky et al. |
| 9,402,678 | B2 | 8/2016 | Slatkine |
| 2001/0020167 | A1 | 9/2001 | Woloszko et al. |
| 2002/0120260 | A1 | 8/2002 | Morris et al. |
| 2002/0169394 | A1 | 11/2002 | Eppstein et al. |
| 2003/0092982 | A1 | 5/2003 | Eppstein |
| 2003/0097126 | A1 | 5/2003 | Woloszko et al. |
| 2003/0109802 | A1 | 6/2003 | Laeseke et al. |
| 2003/0212396 | A1 | 11/2003 | Eggers et al. |
| 2003/0216717 | A1 | 11/2003 | Nahen et al. |
| 2004/0181214 | A1 | 9/2004 | Garabedian et al. |
| 2004/0225286 | A1 | 11/2004 | Elliott |
| 2006/0024358 | A1 | 2/2006 | Santini et al. |
| 2006/0084942 | A1 | 4/2006 | Kim et al. |
| 2006/0095103 | A1 | 5/2006 | Eggers et al. |
| 2006/0167445 | A1 * | 7/2006 | Shafirstein ............ A61B 18/082 606/28 |
| 2007/0149991 | A1 | 6/2007 | Mulholland |
| 2007/0167918 | A1 | 7/2007 | Reed et al. |
| 2007/0191827 | A1 | 8/2007 | Lischinsky et al. |
| 2008/0039832 | A1 | 2/2008 | Palanker et al. |
| 2008/0082090 | A1 | 4/2008 | Manstein |
| 2008/0091182 | A1 | 4/2008 | Mehta et al. |
| 2008/0091183 | A1 | 4/2008 | Knopp et al. |
| 2008/0091184 | A1 | 4/2008 | Knopp et al. |
| 2008/0091185 | A1 | 4/2008 | McGill et al. |
| 2008/0097558 | A1 | 4/2008 | Eggers et al. |
| 2008/0119761 | A1 | 5/2008 | Boecker et al. |
| 2008/0125775 | A1 | 5/2008 | Morris |
| 2008/0154254 | A1 | 6/2008 | Burger et al. |
| 2008/0200914 | A1 * | 8/2008 | Hanlon ............... A61B 18/1442 606/48 |
| 2008/0215039 | A1 | 9/2008 | Slatkine et al. |
| 2008/0281389 | A1 | 11/2008 | Knopp et al. |
| 2008/0312647 | A1 | 12/2008 | Knopp et al. |
| 2009/0036958 | A1 | 2/2009 | Mehta et al. |
| 2009/0099534 | A1 | 4/2009 | Lee et al. |
| 2009/0112205 | A1 | 4/2009 | McGill et al. |
| 2009/0156958 | A1 | 6/2009 | Mehta et al. |
| 2009/0222000 | A1 | 9/2009 | Pacey |
| 2009/0234214 | A1 | 9/2009 | Santini et al. |
| 2009/0275899 | A1 | 11/2009 | Deem et al. |
| 2009/0299361 | A1 | 12/2009 | Flyash et al. |
| 2009/0326571 | A1 | 12/2009 | Mulholland |
| 2010/0010480 | A1 | 1/2010 | Mehta et al. |
| 2010/0081987 | A1 * | 4/2010 | Christian ............ A61B 18/1492 604/21 |
| 2010/0121307 | A1 | 5/2010 | Lockard et al. |
| 2010/0217253 | A1 | 8/2010 | Mehta |
| 2010/0217254 | A1 | 8/2010 | Mehta |
| 2010/0228243 | A1 | 9/2010 | Mehta |
| 2010/0262135 | A1 | 10/2010 | Berube |
| 2011/0028970 | A1 | 2/2011 | Woloszko et al. |
| 2011/0137386 | A1 * | 6/2011 | Kreindel ............... A61B 18/14 607/96 |
| 2011/0264084 | A1 | 10/2011 | Reid |
| 2011/0288543 | A1 | 11/2011 | Cheng et al. |
| 2012/0123401 | A1 * | 5/2012 | Slatkine ............... A61B 18/08 606/28 |
| 2012/0143178 | A9 | 6/2012 | Mehta |
| 2012/0158100 | A1 * | 6/2012 | Schomacker ....... A61B 18/1477 607/101 |
| 2012/0185029 | A1 | 7/2012 | Flyash et al. |
| 2012/0330295 | A1 | 12/2012 | Manwaring et al. |
| 2013/0123767 | A1 | 5/2013 | Clark, III et al. |
| 2013/0184609 | A1 | 7/2013 | Lee et al. |
| 2013/0197473 | A1 | 8/2013 | McMillan |
| 2014/0171934 | A1 | 6/2014 | Flyash et al. |
| 2016/0331440 | A1 | 11/2016 | Slatkine |
| 2017/0281256 | A1 | 10/2017 | Slatkine et al. |
| 2017/0281266 | A1 | 10/2017 | Slatkine et al. |

FOREIGN PATENT DOCUMENTS

| | | |
|---|---|---|
| EP | 1905516 | 4/2008 |
| EP | 2666424 | 11/2013 |
| FR | 2911059 | 7/2008 |
| JP | 03-063045 | 3/1991 |
| JP | 2006-192285 | 7/2006 |
| JP | 2007-531578 | 11/2007 |
| KR | 10-2009-0052631 | 5/2009 |
| KR | 10-0946363 | 3/2010 |
| WO | WO 91/10405 | 7/1991 |
| WO | WO 97/07734 | 3/1997 |
| WO | WO 2005/030071 | 4/2005 |
| WO | WO 2005/096979 | 10/2005 |
| WO | WO 2008/100118 | 8/2008 |
| WO | WO 2010/137885 | 12/2010 |
| WO | WO 2011/013118 | 2/2011 |
| WO | WO 2015/092791 | 6/2015 |
| WO | WO 2016/042546 | 3/2016 |
| WO | WO 2016/042547 | 3/2016 |

OTHER PUBLICATIONS

Applicant-Initiated Interview Summary dated Jul. 13, 2015 From the Re. U.S. Appl. No. 13/386,697.

(56) References Cited

OTHER PUBLICATIONS

Communication Reltaing to the Results of the Partial International Search dated Dec. 3, 2010 From the International Searching Authority Re. Application No. PCT/IL2010/000588.
Communication Relating to the Results of the Partial International Search dated Feb. 5, 2016 From the International Searching Authority Re. Application No. PCT/IL2015/050924.
Examiner-Initiated Interview Summary and Advisory Action Before the Filing of An Appeal Brief dated Spe. 8, 2015 From the Re. U.S. Appl. No. 13/386,697.
International Preliminary Report on Patentability dated Feb. 9, 2012 From the International Bureau of WIPO Re. Application No. PCT/IL2010/000588.
International Preliminary Report on Patentability dated Jun. 30, 2016 From the International Bureau of WIPO Re. Application No. PCT/IL2014/51103.
International Search Report and the Written Opinion dated Mar. 4, 2011 From the International Searching Authority Re. Application No. PCT/IL2010/000588.
International Search Report and the Written Opinion dated Jan. 8, 2016 From the International Searching Authority Re. Application No. PCT/IL2015/050925.
International Search Report and the Written Opinion dated Apr. 14, 2016 From the International Searching Authority Re. Application No. PCT/IL2015/050924.
International Search Report and the Written Opinion dated Jul. 22, 2015 From the International Searching Authority Re. Application No. PCT/IL2014/51103.
Invitation to Pay Additional Fees dated May 13, 2015 From the International Searching Authority Re. Application No. PCT/IL2014/051103.
Notice of Allowance dated Mar. 29, 2016 From the Re. U.S. Appl. No. 13/386,697.
Notice of Reason for Rejection dated Apr. 4, 2014 From the Patent Office of Japan Re. Application No. 2012-522334 and Its Translation Into English.
Notice of Reason for Rejection dated Nov. 7, 2014 From the Patent Office of Japan Re. Application No. 2012-522334 and Its Translation Into English.
Office Action and Search Report dated Jul. 31, 2012 From the Israel Patent Office Re. Application No. 200081 and Its Translation Into English.
Office Action dated Feb. 2, 2014 From the Israel Patent Office Re. Application No. 217734 and Its Translation Into English.
Office Action dated Aug. 5, 2012 From the Israel Patent Office Re. Application No. 201246 and Its Translation Into English.
Office Action dated Dec. 14, 2014 From the Israel Patent Office Re. Application No. 217734.
Official Action dated Apr. 6, 2015 From the Re. U.S. Appl. No. 13/386,697.
Official Action dated Nov. 6, 2014 From the Re. U.S. Appl. No. 13/386,697.
Restriction Official Action dated Aug. 29, 2014 From the Re. U.S. Appl. No. 13/386,697.
Translation dated Jan. 15, 2015 of Office Action dated Dec. 14, 2014 From the Israel Patent Office Re. Application No. 217734.
Chernoff et al. "SilkTouch: A New Technology for Skin Resurfacing in Aesthetic Surgery", Journal of Clinical Laser Medicine & Surgery, 13(2): 97-100, 1995.
Dornier "Dornier Medials Fibertom 8100", Dornier MedTech, Product Sheet, 4 P., Feb. 2007.
Fee "Use of the Shaw Scalpel in Head and Neck Surgery", Otolaryngology—Head and Neck Surgery, 89(4): 515-519, Jul.-Aug. 1981.
Lowe et al. "Skin Resurfacing With the Ultrapulse Carbon Dioxide Laser. Observations on 100 Patients", Dermatologic Surgery, 21(12): 1025-1029, Dec. 1995.
Mestel "M3A10 Viscous Flow: Lubrication Theory—Flow in Thin Films", Graduate Course on Viscous Flow in Imperial College, London, UK, 4 P., 2013.
Park et al. "The Effect of Heat on Skin Permeability", International Journal of Pharmacology, 359(1-2): 94-103, Jul. 9, 2008.
PhotoMedex "Delivery Systems and Accessories for the SLT Contact Laser™ System", Surgical Laser Technology, PhotoMedex Inc., Catalog, 8 P., 2007.
Reed "Preventing Patient Thermal Burns From Electrosurgical Instruments", Reprint of Infection Control Today, 3 P., 2013.
Notification of Office Action dated Nov. 29, 2017 From the State Intellectual Property Office of the People's Republic of China Re. Application No. 201480074496.5 and Its Translation Into English. (9 Pages).
Communication Pursuant to Article 94(3) EPC dated Apr. 16, 2018 From the European Patent Office Re. Application No. 14871250.8. (8 Pages).
Supplementary European Search Report and the European Search Opinion dated Aug. 4, 2017 From the European Patent Office Re. Application No. 14871250.8. (7 Pages).
Communication Pursuant to Article 94(3) EPC dated Jun. 8, 2018 From the European Patent Office Re. Application No. 10747084.1. (5 Pages).
International Preliminary Report on Patentability dated Mar. 30, 2017 From the International Bureau of WIPO Re. Application No. PCT/IL2015/050924. (12 Pages).
International Preliminary Report on Patentability dated Mar. 30, 2017 From the International Bureau of WIPO Re. Application No. PCT/IL2015/050925. (10 Pages).
Official Action dated May 25 2018 From the Re. U.S. Appl. No. 15/218,129. (36 pages).

* cited by examiner

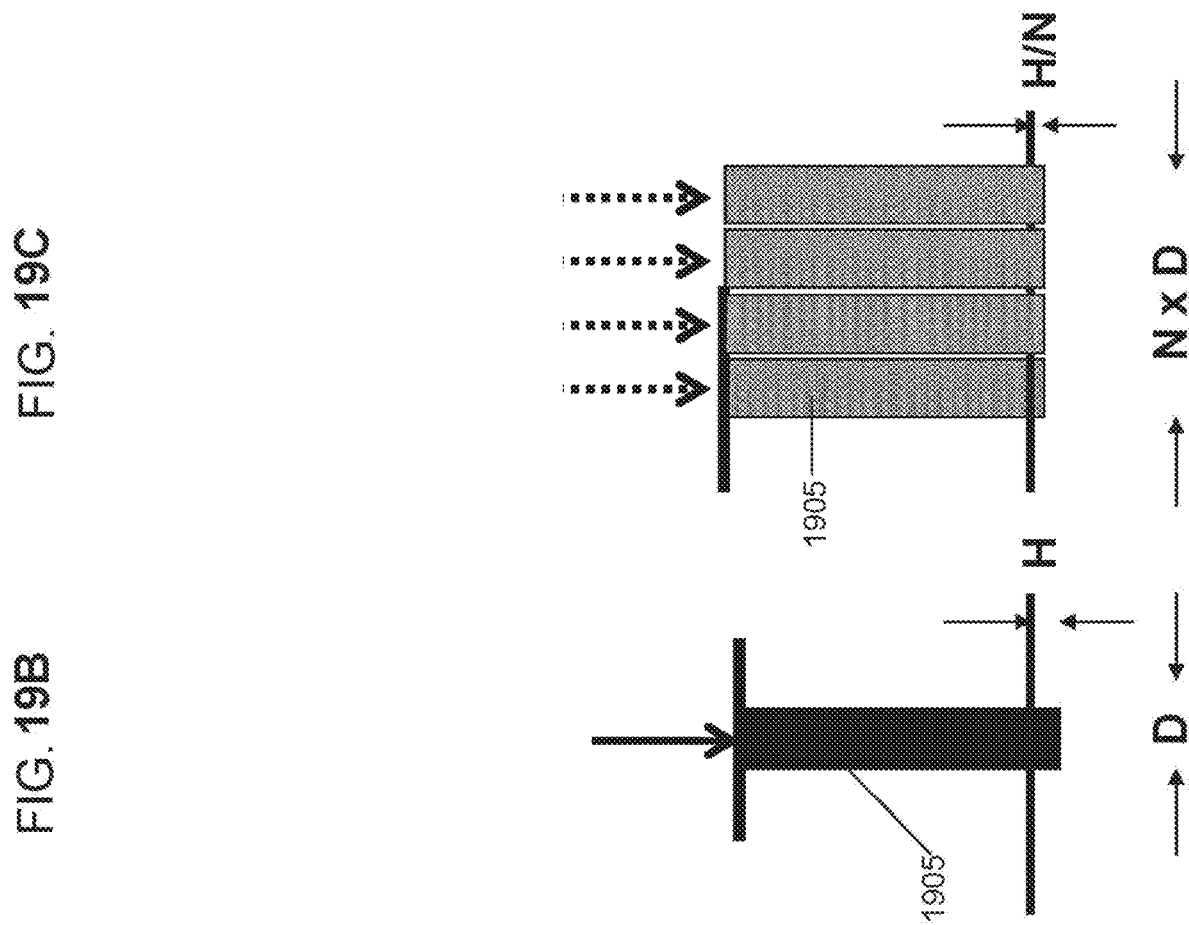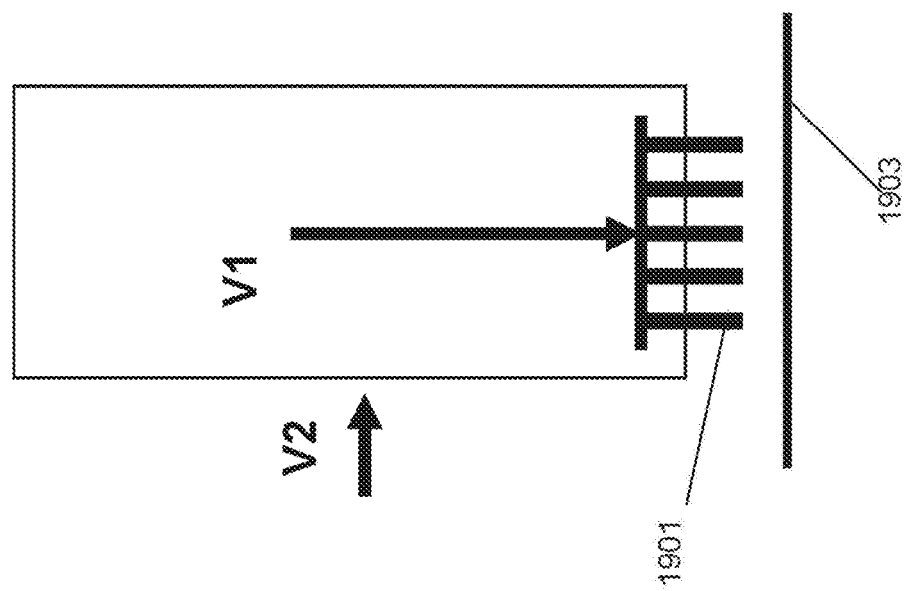

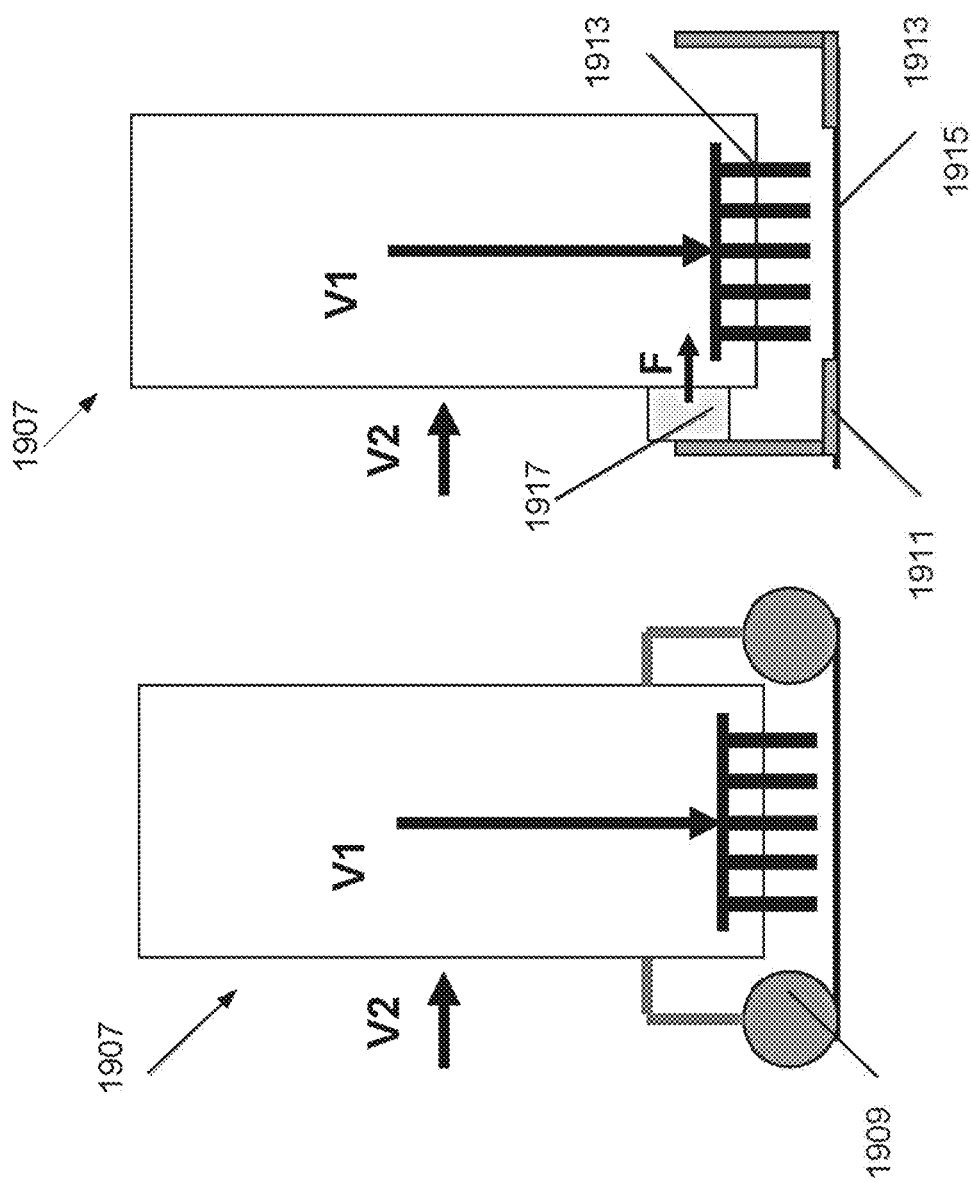
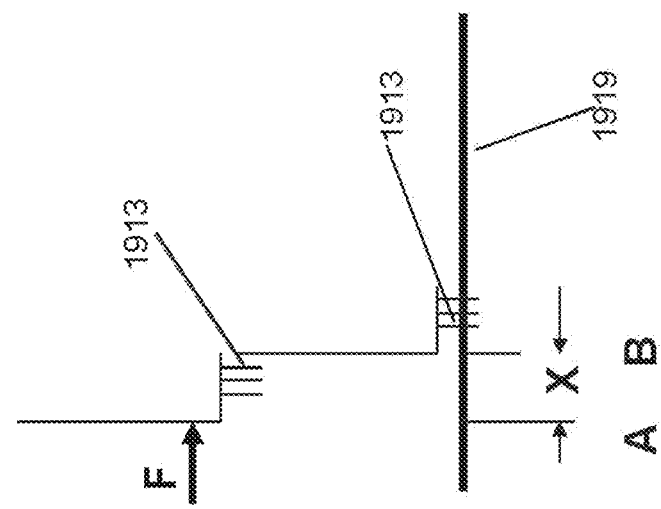
FIG. 19D  FIG. 19E  FIG. 19F

DEVICES AND METHODS FOR TISSUE VAPORIZATION

RELATED APPLICATIONS

This application is related to PCT Patent Application No. PCT/IL2010/000588 filed on Jul. 22, 2010, having Publication No. WO2011/013118, the contents of which are incorporated herein by reference in their entirety.

This application is a National Phase of PCT Patent Application No. PCT/IL2014/051103 having International filing date of Dec. 16, 2014, which claims the benefit of priority under 35 USC § 119(e) of from U.S. Provisional Patent Application No. 61/917,435 filed on Dec. 18, 2013. The contents of the above applications are all incorporated by reference as if fully set forth herein in their entirety.

FIELD AND BACKGROUND OF THE INVENTION

The present invention, in some embodiments thereof, relates to surgical methods and devices, and, more particularly, but not exclusively, to methods and devices for vaporization of tissue.

Various techniques are known to perform tissue ablation, commonly involving the use of a pulsed laser or RF energy.

US Patent Application Publication Number US20040181214 titled "PASSIVELY COOLED ARRAY" to Garabedian et al. discloses "A tissue ablation system includes an elongated shaft, such as a surgical probe shaft, and an needle electrode array mounted to the distal end of the shaft, and an ablation source, such as, e.g., a radio frequency (RF) generator, for providing ablation energy to the electrode array. The tissue ablation system further includes a heat sink disposed within the distal end of the shaft in thermal communication with the needle electrode array. In this manner, thermal energy is drawn away from the needle electrode array, thereby cooling the electrode array and providing a more efficient ablation process.

The tissue ablation system further comprises a coolant flow conduit in fluid communication with the heat sink, so that the thermal energy can be drawn away from the heat sink. In the preferred embodiment, the flow conduit includes a thermal exchange cavity in fluid communication with the heat sink, a cooling lumen for conveying a cooled medium (such as, e.g., saline at room temperature or below) to the thermal exchange cavity, and a return lumen for conveying a heated medium from the thermal exchange cavity. The tissue ablation system further comprises a pump assembly for conveying the cooled medium through the cooling lumen to the thermal exchange cavity at the distal end of the shaft."

SUMMARY OF THE INVENTION

According to an aspect of some embodiments of the invention there is provided a device for vaporizing at least one hole in tissue, comprising an array of vaporizing elements, one or more heating elements configured to heat the vaporizing elements, wherein a geometry of at least a portion of the vaporizing elements is configured to prevent excessive penetration of other vaporizing elements into the tissue. In some embodiments, the portion of vaporizing elements prevents excessive penetration of other vaporizing elements by having a leading surface area adapted for contact with the tissue that is larger than a leading surface area of the vaporizing elements which are prevented from excessively penetrating the tissue. In some embodiments, a distal tip of a vaporizing element that is shaped to prevent excessive penetration of a second vaporizing element is truncated. Optionally, the truncated vaporizing element is shorter than the second vaporizing element. Optionally, the second vaporizing element comprises a sharp distal tip. In some embodiments, the vaporizing elements are heated to a temperature ranging between 300-600 degrees Celsius. In some embodiments, the vaporizing elements are mounted on a plate. In some embodiments, a depth of penetration of at least a portion of the vaporizing elements with respect to a surface of the tissue is less than 300 μm. In some embodiments, the array produces a lesion pattern comprising a combination of deep and shallow craters in the tissue. In some embodiments, the array produces a plurality of craters in the tissue at a spatial distribution ranging between 2-100 craters/cm^2. In some embodiments, a length of a vaporizing element is larger than a base width of the vaporizing element by a factor smaller than 3:1 to prevent bending of the vaporizing element. Optionally, the device comprises pyramidal shaped vaporizing elements.

Optionally, the device comprises conical vaporizing elements. In some embodiments, the one or more heating elements are operable according to a heating protocol suitable for vaporizing tissue by the vaporizing elements. In some embodiments, the device is adapted for vaporizing a keratin layer in a nail by heating the keratin to a temperature higher than 500 degrees Celsius. In some embodiments, the device is adapted for exposing a surface of scar tissue for applying topical medication.

According to an aspect of some embodiments of the invention there is provided a device for vaporizing at least one hole in tissue, comprising an array of vaporizing elements, one or more heating elements configured to heat the vaporizing elements, the vaporizing element comprising at least one material selected to generate local vaporization and to reduce a damage region when the vaporizing element is heated to a temperature higher than 300° C. Optionally, the material comprises a thermal conduction coefficient greater than 80 Watts per degree Kelvin per meter. In some embodiments, the material reduces diffusion in a second material when the vaporizing element is heated to a temperature higher than 300° C. In some embodiments, the material and/or second material and/or a material coating the second material reduces IR emissivity towards the tissue. Optionally, the first material is silver or nickel, and the second material is copper. In some embodiments, a body of the vaporizing element is made of copper, and a nickel layer covers the copper. In some embodiments, the layers of copper and nickel are coated by a low IR emissivity layer made of gold.

According to an aspect of some embodiments of the invention there is provided a method for self sterilizing an array of vaporizing elements, the array coupled to a heating element, comprising heating the vaporizing elements to a temperature higher than approximately 500 degrees Celsius to remove carbon residue from the vaporizing elements. In some embodiments, the vaporizing elements are heated to a temperature higher than approximately 500 degrees Celsius for a duration ranging between 0.5-5 seconds.

According to an aspect of some embodiments of the invention there is provided a device for vaporizing at least one hole in tissue, comprising a plurality of vaporizing elements arranged in an array; one or more heating elements configured to heat the vaporizing elements; wherein the array of vaporizing elements is adapted for moving in a cyclic movement profile, wherein the vaporizing elements are lowered and elevated repetitively to and from the tissue at an absolute acceleration rate that monotonically increases at least a long 30% of the pathway of said vaporizing elements leading towards the tissue. Optionally, the increasing absolute acceleration rate reaches a maximal value upon contacting the tissue. In some embodiments, the array is operated by a camshaft assembly. Optionally, the camshaft assembly comprises a rotary motor and a lever for generating linear motion of the vaporizing array. In some embodiments, the device and camshaft assembly are configured in a hand held device. Optionally, the hand held device further comprises a control unit. In some embodiments, the control unit is configured for controlling at least one of: a treatment temperature profile of the vaporizing elements, a self-sterilization temperature profile of the vaporizing elements, a penetration distance into the tissue, a dwelling time of the vaporizing elements within the tissue, a velocity of advancing and/or retracting said array, a number of repetitive treatments, a time interval between repetitive treatments, a replacing of the vaporizing elements. In some embodiments, the device is movable in a horizontal direction across the tissue. In some embodiments, the device comprises at least one of wheels and a spring for advancing the array horizontally. Optionally, a penetration depth of the vaporizing elements is reduced by moving the array in parallel to the tissue. In some embodiments, the horizontal movement is operated by a controller.

According to an aspect of some embodiments of the invention there is provided a method for repetitive vaporization of tissue, comprising heating an array of vaporizing elements to vaporize an area in the tissue, elevating the array from the tissue to allow most of the vapors formed during vaporization to escape, and re-applying the array of vaporizing elements to further vaporize the area in tissue.

Optionally, re-applying is performed before the tissue moves. Optionally, re-applying is performed in a time interval shorter than 200 msec from a time point in which said vaporizing elements disengaged the tissue. In some embodiments, the method is repeated to vaporize a deeper layer within the tissue. In some embodiments, the method further comprises applying a vaporizable substance to the tissue prior to vaporizing the tissue. Optionally, the vaporizable substance is liquid or gel.

According to an aspect of some embodiments of the invention there is provided a device for heating tissue, comprising a plurality of thermally conductive elements arranged in a array and configured for contacting the tissue; a heating element configured to heat the vaporizing elements; an RF generator; at least one RF conduit for transmitting RF energy to the tissue. Optionally, the array further comprises electrodes adapted for transmitting RF energy into the tissue. In some embodiments, the device is a hand held device.

According to an aspect of some embodiments of the invention there is provided a device for vaporizing a thin layer of tissue, comprising a vaporizing element shaped as a foil; one or more heating elements configured to heat the vaporizing element; a frame holding the vaporizing element, the frame adapted for moving towards and away from the tissue. In some embodiments, the foil vaporizes a tissue layer having a depth smaller than 20 μm. Optionally, the foil is attached to a spring for advancing and retracting the foil from the tissue. In some embodiments, the device further comprises wheels for rolling the device over a surface of the tissue. In some embodiments, the foil is planar and has a surface area ranging between 0.0001 cm^2-1 cm^2. In some embodiments, the foil has a width smaller than 100 μm for vaporizing an elongated narrow crater in the tissue.

According to an aspect of some embodiments of the invention there is provided a device for vaporizing at least one hole in tissue, comprising one or more vaporizing elements arranged in an array; one or more heating elements configured to heat the vaporizing elements; at least one piezoelectric transducer mechanically coupled to the array to move the vaporizing elements towards at least one of the tissue and the one or more heating elements. In some embodiments, the piezoelectric transducer is coupled to the array by a thermally insulating rod. In some embodiments, the transducers are activated by a controller according to an indication of a distance of the array from the tissue to be treated.

According to an aspect of some embodiments of the invention there is provided a pyramidal shaped element for vaporizing a hole in tissue, comprising a thermally conductive core embedded within a biocompatible material, wherein the length of the element ranges between 1-10 mm. Optionally, the core is formed of copper and the biocompatible material is formed of at least one of titanium and stainless steel.

Optionally, the element is pyramidal shaped. In some embodiments, a length of the core with respect to a total length of the vaporizing element is selected such as to reduce a thermal relaxation time of the element. In some embodiments, the biocompatible material is formed as a sheet having a thickness smaller than 500 μm.

Optionally, the sheet is formed with varying thickness.

As referred to herein, the term "vaporizing" may include producing a hole in tissue by delivering heat to the tissue, which causes one or more effects such as turning the tissue of the hole into vapors, ablating tissue, causing denaturation of the tissue, causing crumbling of the tissue into smaller particles, burning the tissue, engraving the tissue, and/or other effects caused by delivering heat to the tissue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 19A-F describe an exemplary movement profile comprising horizontal and vertical velocity components, according to some embodiments of the invention;

DESCRIPTION OF SPECIFIC EMBODIMENTS OF THE INVENTION

Figure 1A:
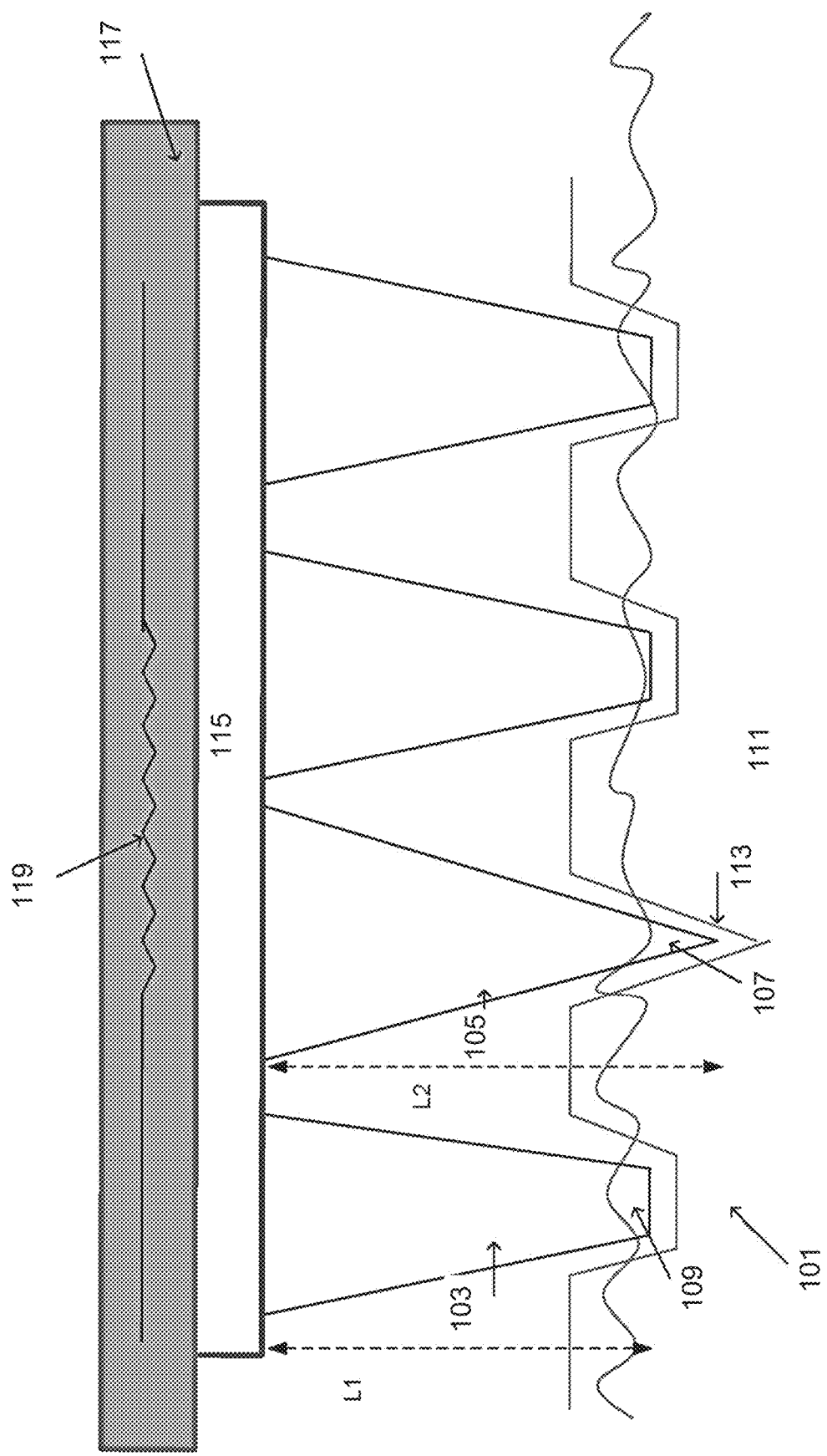
FIGS. 1A-B are a side view and a front view, respectively, of an array of vaporizing elements, according to some embodiments of the invention.

The present invention, in some embodiments thereof, relates to surgical methods and devices, and, more particularly, but not exclusively, to methods and devices for vaporization of tissue.

Some embodiments of the invention relate to a vaporizing element, such as a vaporizing rod, adapted to supply a large amount of heat in a short amount of time to vaporize the tissue, while reducing other types of heat damage such as charring of the tissue. In some embodiments, holes, grooves, craters or indentations are produced in the tissue.

An aspect of some embodiments of the invention relates to an array of vaporizing elements for delivery of heat at a high temperature to a localized area in the tissue, where at least a portion of the vaporizing elements are shaped to prevent excessive penetration of other vaporizing elements into the tissue. In some embodiments, a vaporizing element configured for preventing excessive penetration of a second vaporizing element comprises a leading surface area that is larger than a surface of the second vaporizing element. In some embodiments, an arrangement of the vaporizing elements provides inherent safety during operation, for example by comprising a combination of sharp conical vaporizing rods positioned adjacent truncated vaporizing rods, which limit a movement of the sharp rods deeper into the tissue. In some embodiments, the arrangement of vaporizing elements having different geometries produces a combination of craters of various dimensions, such as various depths, in the tissue. In some embodiments, the vaporizing elements are shaped as pyramids. Optionally, at least a portion of the vaporizing elements comprise a truncated distal end. The cross section area of the truncated elements may affect the dimensions of the crater, for example formed by the non-truncated vaporizing elements.

An aspect of some embodiments relates to an array of vaporizing elements comprising a multi-layer structure which contributes to a performance of the array under high temperatures. In some embodiments, the vaporizing element comprises at least one material selected to generate limited vaporization and to reduce a damage region, when the element is heated to an operating temperature, for example a temperate higher than 400° C. In some embodiments, the material has a thermal conduction coefficient that is greater than 80 Watts per degree Kelvin per meter. In some embodiments, the material reduces diffusion in second material, for example a layer of silver reduces diffusion from an underneath layer of copper. In some embodiments, the material is selected to reduce IR emissivity towards the tissue, for example using gold, which has relatively low IR emissivity, to coat the vaporizing element.

In some embodiments, a middle and/or external layer of a vaporizing element is adapted for maintaining a condition of an internal layer. In some embodiments, an internal layer of the vaporizing element is formed of a heat conductive material such as copper, and the copper is optionally coated by a layer configured for reducing diffusion of the copper ions, often occurring at high temperatures, particularly above 300° C., which is a possible range of temperatures the array is operated at. Optionally, the layer is made of silver. In some embodiments, the silver coated vaporizing elements and/or a surface of a plate onto which the vaporizing elements are mounted is coated with a biocompatible layer, for example a layer of gold and/or rhodium.

Optionally, due to the relatively low IR emissivity properties of gold, the gold layer reduces IR radiation towards a surface of the tissue.

In some embodiments, the heat conductive material such as copper or Aluminum Nitride (ALN) are coated by ceramics or glass, for example providing mechanical protection of the vaporizing elements. The ceramic or glass coating is adapted to withstand high operating temperatures, for example above 400° C.

In some embodiments, as the multi layer structure withstands high temperatures, the array is adapted for self cleaning and/or self sterilizing. In some embodiments, self sterilization is achieved by heating the vaporizing elements to a temperature over 500° C. Optionally, tissue particles and/or carbonized particles that adhered to the vaporizing elements are removed by the self sterilization process, for example as a result of oxidation transforming carbon residue into CO2.

An aspect of some embodiments relates to a cyclic movement profile of an array of vaporizing elements. In some embodiments, the movement profile includes accelerating the array of vaporizing elements to a rate high enough for shortening a dwelling duration of the vaporizing elements within the tissue. In some embodiments, the movement profile includes elevating the tips of the vaporizing elements from the tissue between repetitive treatments, for releasing vapors that are trapped between the tissue and tips of the vaporizing elements. In some embodiments, the cyclic movement profile includes setting a time interval between repetitive treatments that is short enough to prevent tissue movement in between treatments. Optionally, by repetitive and vaporization of an area in the tissue, a deeper crater can be produced. In some embodiments, a camshaft mechanism is utilized for operating the array in a cyclic movement profile. Optionally, the camshaft assembly includes a rotary motor, a wheel, and a lever for generating linear motion of the vaporizing array.

In some embodiments, the vaporizing elements of the array are moved together. Alternatively, one or more vaporizing elements are moved independently of other elements.

In some embodiments, the array is movable in a horizontal direction.

Optionally, moving the array vertically and horizontally, a penetration depth of the array may be reduced. In some embodiments, the horizontal movement provides for increasing a width of a crater formed in the tissue.

An aspect of some embodiments relates to a vaporizing array connected to an RF generator. Optionally, the vaporizing elements of the array are adapted for transmitting RF energy to the tissue. Additionally or alternatively, different RF electrodes are used, for example being mounted to the same plate that the vaporizing elements are mounted on.

In some embodiments, a vaporizing element is shaped as a thin foil, adapted to vaporize a thin layer of tissue, for example a crater having a maximal depth of 20 μm with respect to the uppermost surface of tissue.

In some embodiments, a lesion pattern of elongated, narrow craters is produced in the tissue. Optionally, the pattern of elongated, narrow craters is obtained by using one or more vaporizing elements shaped as a wire. In some embodiments, a plurality of wires are assembled on a device configured for rolling on a surface of the tissue, for forming a lesion pattern of elongated, narrow craters.

In some embodiments, the vaporizing array and/or a single vaporizing element is incorporated in a hand held device. Optionally, the hand held device comprises a control unit, for controlling parameters related to vaporizing tissue and/or to limiting damage to the tissue, such as the treatment temperature profile, a penetration depth of the vaporizing elements in the tissue, a motion profile of the vaporizing elements, a dwelling duration of the element in the tissue, a time interval between repetitive treatment pulses.

An aspect of some embodiments relates to a vaporizing array assembly comprising one or more piezoelectric transducers. In some embodiments, the transducers are mechanically coupled to the array and configured to move the array towards the tissue and/or towards the heating element, be deforming in response to electrical activation. Optionally, the transducers are activated by a controller, for example according to an indication of a distance of the array from the tissue to be treated.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

An Array of Vaporizing Elements

Figure 1B:
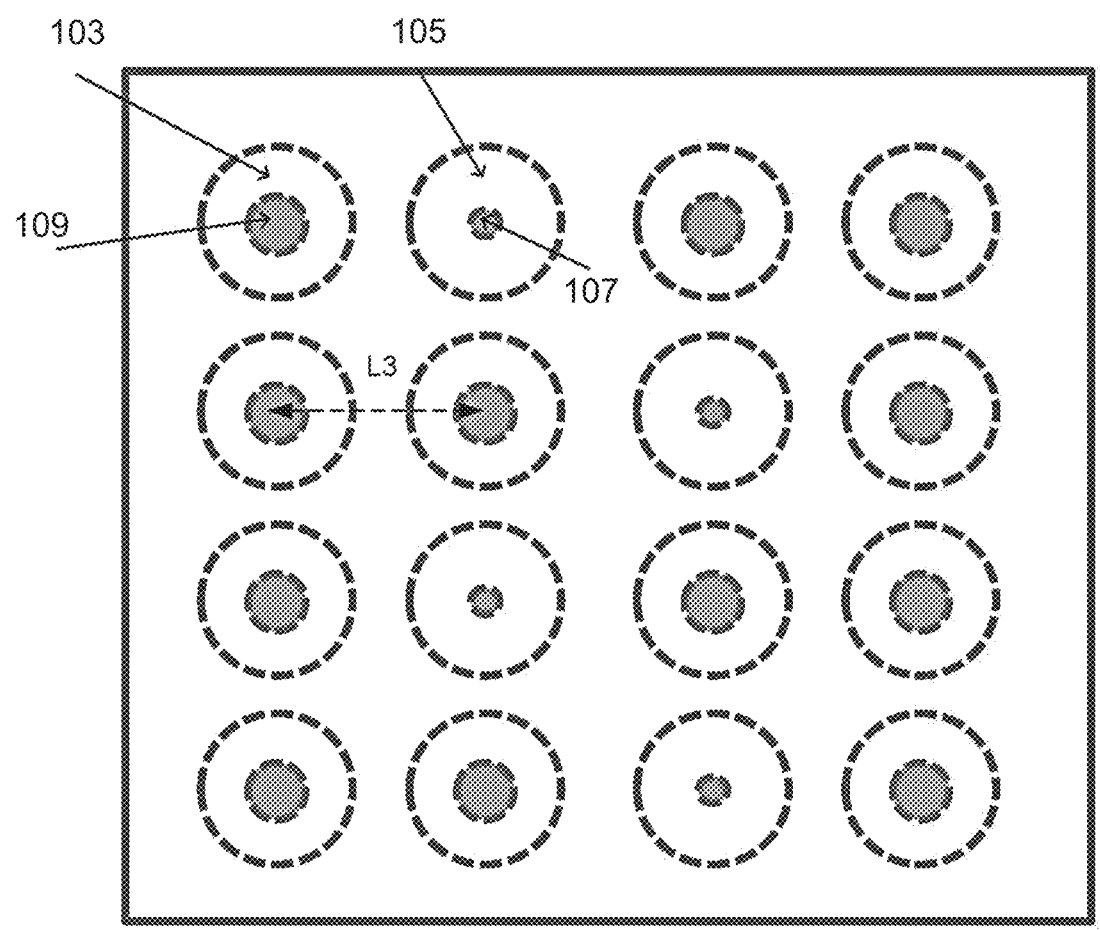

Referring now to the drawings, FIGS. 1A-B are a side view and a front view, respectively, of an array of vaporizing elements, according to some embodiments of the invention.

In some embodiments, array 101 comprises at least one vaporizing element, such as conical rod 103 and/or conical rod 105. In some embodiments, a vaporizing element is adapted to supply a large amount of heat, in a short amount of time, to vaporize at least a portion of tissue 111. In some embodiments, holes, grooves, indentations and/or craters are produced in tissue 111.

In order to vaporize tissue while not destroying tissue which should not be vaporized, the present invention, in some embodiments thereof, teaches applying heat at a high temperature to a localized area in tissue. In some embodiments, the temperature should be high enough to rapidly vaporize the tissue, that is, a temperature above 100 degrees Celsius, which is a boiling temperature of water, which is a major constituent of tissue. Preferably, the temperature should be higher than approximately 200 degrees Celsius, for example ranging between 200-600 degrees Celsius, for example 300, 400, 450, or 500 degrees Celsius.

In some embodiments, due to the high temperature profile, bleeding of the vaporized tissue is reduced. In some embodiments, due the high temperature profile, craters are formed with defined borders, and collateral damage is reduced. For example, damage surrounding the formed crater can be limited to an extent less than 10 μm, less than 5 μm, less than 1μ or intermediate, larger or smaller extents from the periphery of the crater.

In some embodiments, the heat capacity of the vaporizing element should be such that a tip such as tip 107 of the vaporizing element which is adjacent to the tissue contains an amount of heat which is enough to vaporize tissue 113 which is adjacent to the tip. The amount of heat necessary to vaporize tissue is dependent on the volume to be vaporized. The volume to be vaporized approximately equals a cross section of the tip, multiplied by the depth which is to be vaporized. In the case of a sharp pyramidal tip, the vaporized volume is one third of that multiplication, resulting in the capability to vaporize deeper craters with same width and same energy.

In some embodiments, the vaporizing elements such as elements 103, 105 are bonded to a plate 115, for example soldered and/or adhesively bonded and/or mechanically bonded for example using pins or screws to plate 115.

In some embodiments, plate 115 is coupled to a heating element 117. In some embodiments, the heating element is a high temperature foil, an electrically heated wire, an optical heat source, a metallic heating element, and/or any other heating element suitable for heating the vaporizing elements to a temperature ranging between 200-600 degrees Celsius. In some embodiments, heating element 117, for example being a foil, is heated by an electrical resistor 119.

In some embodiments, the vaporizing device comprises a single vaporizing element. Alternatively, the vaporizing device comprises an array of vaporizing elements, for example between 2-20 vaporizing elements, such as 8 elements, 10 elements, 16 elements, or any intermediate, higher or smaller number of elements.

Various vaporizing elements may comprise different shapes, for example a vaporizing element may have a conical profile, a circular profile, a rectangular profile, a pyramidal profile, a trapezoidal profile, or any other shape. This figure, for example, shows vaporizing elements such as 103 and 105 having a conical profile. Optionally, a single array comprises elements of various shapes.

In some embodiments, at least a portion of the vaporizing elements are configured for preventing excessive penetration of other vaporizing elements, for example by the vaporizing element having a leading surface area adapted for contact with tissue that is larger than a leading surface area of a different vaporizing element which is prevented from further penetrating the tissue. For example, a leading surface of vaporizing element 103 (pointed to by 109 in FIG. 1B) is larger than a leading surface area of vaporizing element 105 (pointed to by 107 in FIG. 1B), for example 20%, 50%, 75% 90% or intermediate, larger or smaller percentages larger. Optionally, the size of the leading surface area of, for example, element 103 is determined according to the desired penetration depth of, for example, element 105. Optionally, the larger the leading surface is, the more resistance applied by the surface of the tissue, preventing additional penetration of at least some of the elements.

In some embodiments, a vaporizing element such as element 105 comprises a sharp tip 107 adapted for penetrating into the tissue. Alternatively, a vaporizing element such as element 103 comprises a blunt, truncated tip, such as tip 109. In some embodiments, truncated element 103 is configured for abutting against a surface of the tissue. Additionally or alternatively, truncated element 103 is configured for pushing against a surface of the tissue. Additionally or alternatively, truncated element is configured for forming a crater that is shallower than, for example, a crater formed by element 105.

In some embodiments, array 101 comprises a combination of sharp and truncated elements. Optionally, vaporizing elements such as truncated element 103 prevent excessive penetration of elements such as sharp element 107 to a deep tissue layer. Optionally, the combination of sharp and truncated elements limits a movement of the array as it is introduced onto the tissue, for example onto skin, thereby providing an inherent safety mechanism. In some embodiments, dimensions of a crater formed in the tissue can be predicted, for example a maximal depth can be determined according to a difference between the length of, for example, sharp vaporizing element 105 (having a length L2) and truncated vaporizing element 103 (having a length L1).

In some embodiments, array 101 comprises a combination of vaporizing elements having various lengths. Optionally, craters with different depths are formed when elements of different lengths are used. For example, as shown in this figure, element 103 having a length L1 is shorter than element 105 having a length L2. In some embodiments, a length of a vaporizing element ranges between 1-10 mm.

In some embodiments, vaporizing elements advance between 50 μm to 500 μm into the tissue, in the vaporizing phase.

In some embodiments, array 101 comprises a combination of vaporizing elements having various geometrical profiles and/or cross section areas. Optionally, craters are formed with different cross section areas and/or different volumes and/or different geometrical profiles, optionally complying with the dimensions of the vaporizing elements.

In some embodiments, an arrangement of array 101 is determined such as to produce a certain lesion pattern, for example to form craters having a predetermined distance between them. For example, as shown in FIG. 1B, distances such as L3 between tips of the vaporizing elements are determined to form craters having a similar distance L3 between their centers. In some embodiments, a distance L3 between adjacent tips (and/or distal end surfaces, and/or a tip and a distal end surface) of the vaporizing elements ranges between 0.5 mm -1.5 mm.

In some embodiments, an arrangement of the array is provided such as to form a certain spatial distribution of craters in the tissue. In an example, the vaporizing array arrangement can be provided such as to form craters at a spatial distribution of 2-100 craters/cm^2. In some embodiments, an arrangement of the vaporizing elements of array 101 is provided to form deep craters surrounded by shallow indentations, and/or any other lesion patterns.

In some embodiments, a crater depth, as measured from an external surface of the tissue, ranges, for example, between 1-200 μm. In some embodiments, a crater depth is identical to the penetration depth of the vaporizing element. It should be noted that in some cases, the crater depth is not necessarily identical to the penetration depth of the vaporizing element, as heat is diffused from the element into the tissue and may vaporize tissue ahead of the vaporizing element.

In some embodiments, the vaporizing elements are heated by heating element 117 through plate 115. In some embodiments, a coupling between plate 115 and heating element 117 allows fast transfer of heat from heating element 117 to plate 115.

Optionally, surfaces of the plate 115 and/or heating element 117 directed towards each other are flat so that a minimal gap is formed between them, increasing the rate of heat transfer. For example, a surface of the plate and/or a surface of the heating element are made with a height tolerance smaller than 30 μm, as calculated over, for example, a 1 cm^2 area, to enlarge an area of contact between the surfaces.

Optionally, the heat transfer rate is sufficient to provide a rate of 1 treatment per second (i.e. a single application of the array to the treated tissue). For example, the heat transfer rate between heating element 117 and plate 115 is at least 1 Joule per second. In some embodiments, one or more heating elements 117 are operable at a protocol suitable for vaporizing tissue by the vaporizing elements. Optionally, the heat transfer rate from the one or more heating elements is high enough to provide for the vaporizing elements to effectively heat the tissue at a relatively short amount of time.

In some embodiments, the plate and vaporizing elements assembly and/or only a portion of it, such as the tips of the vaporizing elements, is heated to approximately 500 degrees Celsius within less than 1 sec.

By way of a non-limiting example, in order to vaporize an area of 100 microns by 100 microns, to a depth of 100 microns, approximately 3 milliJoules of heat are needed, based on the vaporization energy of water which is approximately 3,000 Joule/cm³. It is noted that the heat needed to vaporize tissue is substantially close to the heat needed to vaporize water, since tissue thermal parameters are very similar to water thermal parameters.

In order to supply the heat to the tissue, the heat relaxation time of the vaporizing element, should be such that the heat can come rapidly to the surface of the tip of the vaporizing element. It is noted that the heat relaxation time depends, among other factors, on heat conductivity, heat capacity, and geometric dimensions, such as length, of the vaporizing element.

The heat supply should be fast enough to vaporize the adjacent tissue without allowing too much heat to diffuse into the tissue, that is, a heat relaxation time substantially shorter than that which produces an allowed or planned necrosis depth in tissue. By way of approximation, the heat relaxation time should be substantially shorter than that of water.

In some embodiments, the vaporizing element (or, alternatively, an array of vaporizing elements) is "flicked" onto the tissue for a very short and limited amount of time. The flicking keeps the vaporizing element adjacent, optionally in contact, to the tissue for only a short time, limiting time for heat conductance into tissue, and limiting collateral damage to acceptable levels.

In some embodiments, the vaporizing element is considered as providing heat to the tissue as long as the vaporizing element is adjacent to the tissue. In some embodiments, the vaporizing element is considered as providing heat to the tissue as long as the vaporizing element is within the volume of the crater.

In order to provide heat rapidly to the tissue, a vaporizing element comprises at least one material allowing fast thermal conduction. In some embodiments, the vaporizing element includes material having a thermal conduction coefficient greater than 80 Watts per degree Kelvin per meter. In some embodiments, the vaporizing element includes material having a specific heat capacity greater than 0.3 kiloJoules per kilogram per degree Kelvin. In some embodiments, the vaporizing element includes a material with heat conductivity equal to or higher than heat conductivity of copper. In some embodiments, the vaporizing element includes a material with specific heat capacity equal to or higher than specific heat capacity of copper. Some materials, such as some metals, have thermal conductivity as high as, by way of a non-limiting example, copper, enable such rapid heat flow. In some embodiments, the vaporizing element includes a material with a heat conduction coefficient equal to or greater than the heat conduction coefficient of stainless steel.

In some embodiments, for example when creation of extremely shallow craters is advantageous, the vaporizing elements may comprise a material having heat conductivity equal to or lower than the heat conductivity of glass.

In some embodiments, vaporizing elements of different materials are combined together, for example in a single array. For example, a portion of the vaporizing elements of an array are made of copper, and a second portion of the vaporizing elements of an array are made of stainless steel. Optionally, due to different heat conduction properties of the materials, craters of various depths can be formed in the tissue. For example, elements made of stainless steel, having a thermal conductivity about $\frac{1}{30}^{th}$ of that of copper, may form shallower craters than those formed by the copper elements. A potential advantage includes modifying the treatment 'aggressiveness' by combining vaporizing elements of different materials, for example in a single array.

In some embodiments, when applying a vaporizing element to the tissue, the tissue is stretched. Optionally, stretching ensures homogenous contact with the tissue, as further disclosed by PCT publication number WO2011/013118.

In some embodiments, the vaporizing elements are applied to the tissue for treating various conditions, for example aesthetic applications such as treating wrinkles and/or scars on the skin, performing skin resurfacing or skin rejuvenation, treating nail tissue, and/or treating other tissue such as treatment of oral, nasal or ear cavities, treatment of the ear drum, treatment of vocal cords, treatment of respiratory system tissue, esophagus tissue, vaginal tissue, abdominal tissue.

Various Configurations of an Array of Vaporizing Elements

FIGS. 2A-D show various array configurations, according to some embodiments of the invention.

Figure 2A:
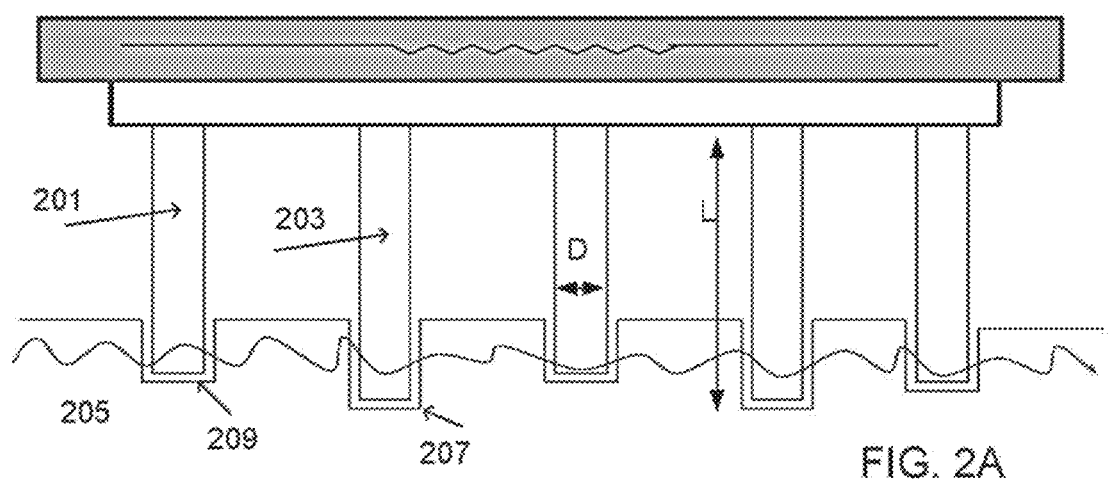
FIGS. 2A-D are exemplary array configurations, according to some embodiments of the invention.
Figure 2B:
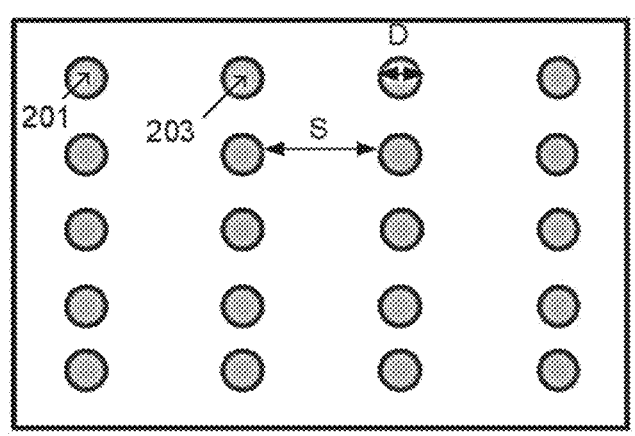

FIG. 2A is a side view and FIG. 2B is a front view of an array comprising vaporizing elements shaped as cylindrical rods, such as rods 201 and 203. In some embodiments, at least a portion of the rods are shorter than others, for example rod 201 is shorter than rod 203. In some embodiments, the rods form craters having various depths, such as crater 209 and deeper crater 207.

In some embodiments, dimensions of the rods are determined according to the type of treatment. For some implementations, such as skin resurfacing, an array such as the array shown in FIG. 2B comprising 4×5 rods, for example having a diameter D of 200-300 µm, and a distance S of 700-800 µm in between the rods may be used. Optionally, in this case, the rod length L may range between 0.7-1.5 mm, for example 1 mm for the short rods such as 201, and 1.2 mm for the long rods such as 203. In another example, the difference between a long rod and a short rod may range between, for example, 50-300 µm, such as 100 µm, 200 µm.

Figure 2C:
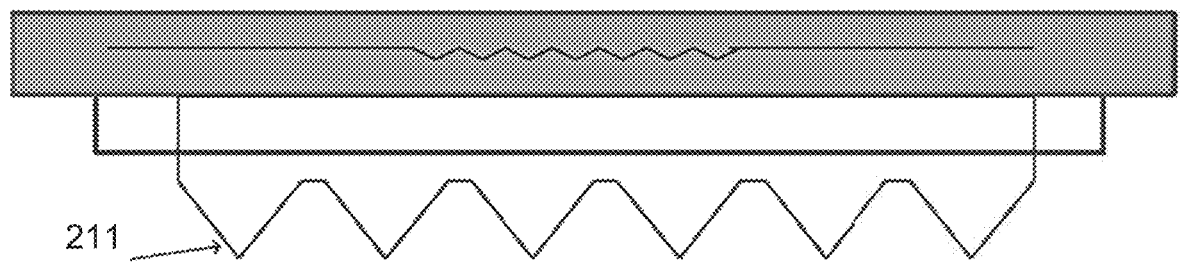
Figure 2D:
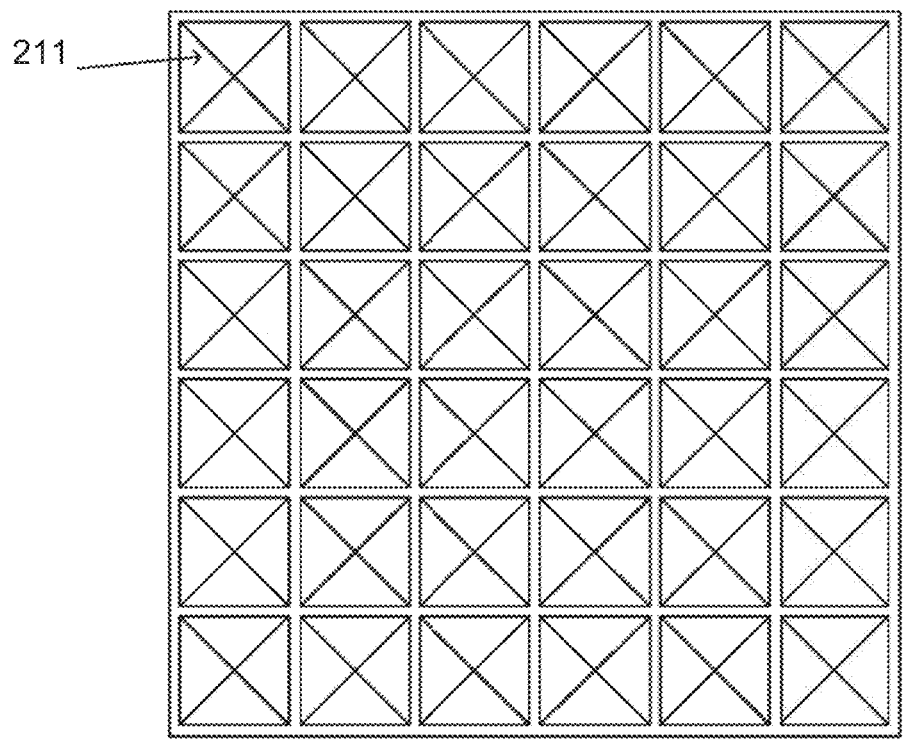

FIG. 2C is a side view and FIG. 2D is a front view of an array comprising vaporizing elements shaped as pyramids 211. In some embodiments, for example as shown in this figure, the vaporizing pyramids are equally sized. Alternatively, the vaporizing elements may comprise different sizes, for example different lengths.

In some embodiments, dimensions of a vaporizing element are defined to prevent possible bending of the element, which may occur as a result of heating the vaporizing element to a high temperature. A vaporizing element may gradually bend, for example as a result of softening of the metal comprising the vaporizing element, such as softening of copper. Optionally, bending occurs as a result of multiple treatments, where the vaporizing element is heated, cooled, and heated again.

Optionally, bending is affected by an angle formed between a vaporizing element (or an array of elements) and the tissue. It is possible that by positioning the vaporizing element perpendicularly to the tissue, such that an angle of approximately 90° is formed between the tissue and the vaporizing element, bending of the vaporizing element is reduced. Optionally, bending over time causes displacement of the distal ends of the vaporizing elements, and may result in misplaced crater formation. For example, when repetitive treatment is applied, the vaporizing elements may not contact the same tissue area that they previously contacted, and an area of healthy tissue between the craters may be damaged.

In some embodiments, a ratio between a length of the vaporizing element and a width of its base has been found to affect the bending. The inventors have concluded that the ratio between the length of the vaporizing element and a width of the base for example in the case of copper elements that are heated to an operating temperature of 400° C., should range between 1:1 to 1:5. A potential advantage of the pyramidal shape element, in view of the bending phenomena, is the ability to use a relatively sharp tip, for example having a width of 150-200 µm at a distal surface, with a relatively long body, for example having a height of 1.2 mm.

In experiments conducted by the inventors, 5 mm long rods having a 500 µm base width (i.e. having a ratio of 1:10) were heated to 400 degrees Celsius to treat a 1×1 cm^2 area of tissue, 20 times. At the end of operation, some bending was observed on the rods.

On the other hand, rods having a length of 1.23 mm and a base width of 1.25 mm did not show bending at all.

In another example, a copper pyramidal element having 1.25 mm base width, a length (height) of 1.25 mm, and a width of 200 micron at a surface of the distal tip, did not show bending as well.

A System for Vaporizing Tissue Using an Array of Vaporizing Elements

Figure 3:
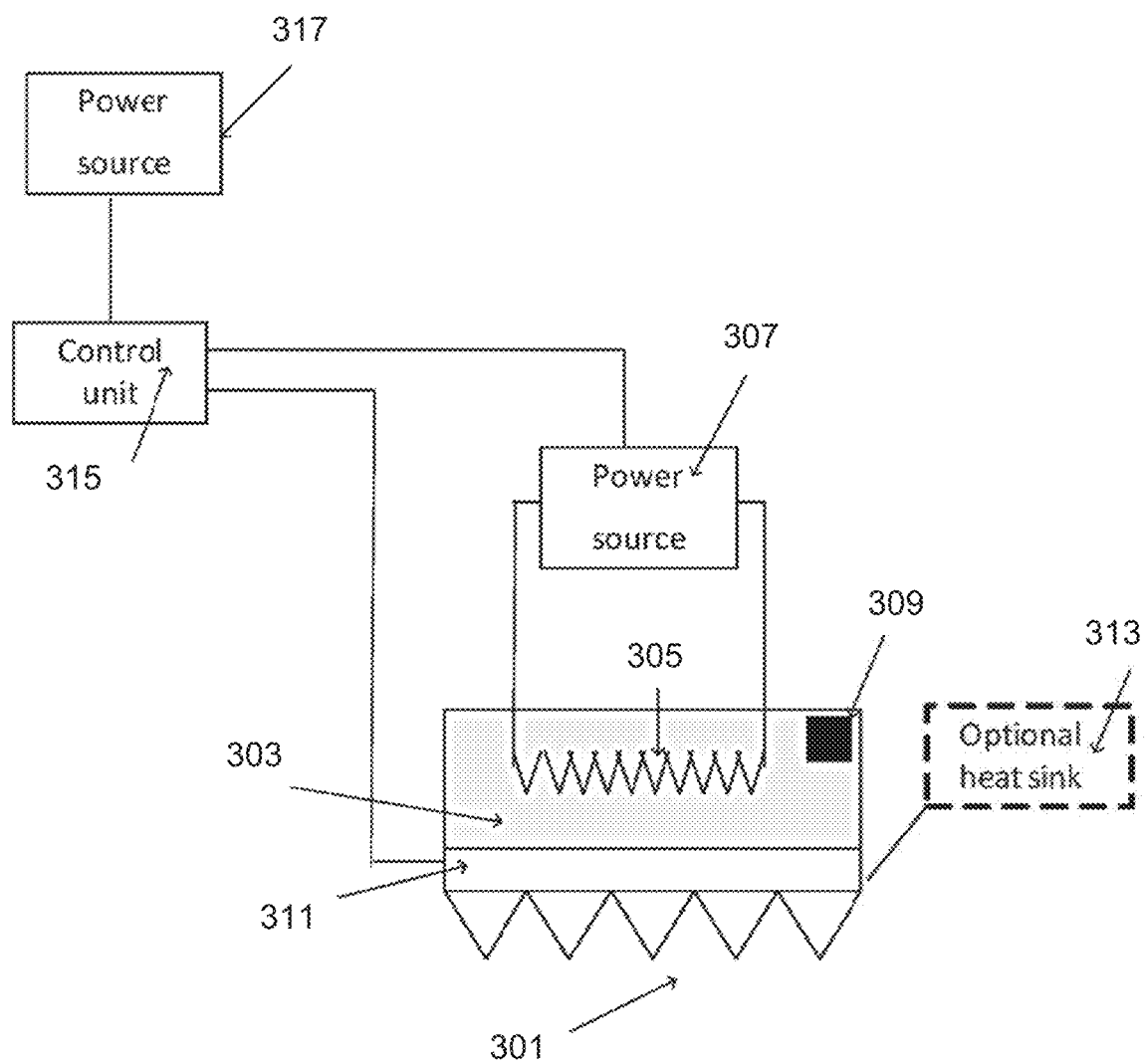
FIG. 3 is a block diagram of a system for vaporizing tissue using a vaporizing element or an array of vaporizing elements, according to some embodiments of the invention.

FIG. 3 is a block diagram of a system for vaporizing tissue using a vaporizing element or an array of vaporizing elements, according to some embodiments of the invention.

In some embodiments, an array of vaporizing elements 301 is coupled to a heating element 303. Optionally, heating element 303 has a planar configuration, for example being a foil. Optionally, heating element 303 has a cylindrical configuration, and/or any other shape.

Heating element 303 is optionally heated by an electrical resistor 305 and/or by any other means, such as an optically heated source, an ultrasound source, or an exothermic chemical reaction.

In some embodiments, electrical resistor 305 is connected by an electrical circuit to a power source 307, for example a battery or a power connection such as a 50/60 Hz supply line. Optionally, the heating element can be separated from the power supply, for example a decoupling mechanism may be utilized between multiple treatments to disconnect heating element 303 from power source 307. In some embodiments the vaporizing elements are electrically insulated from the electric power supply, also so as not to produce an electrical contact with the tissue being vaporized.

In some embodiments, the vaporizing array 301 is heated by a wireless heating method, such as optical heating by light waves, or heating by microwaves.

In some embodiments, heating element 303 comprises a temperature sensor 309, such as a thermistor or a thermocouple, for monitoring a temperature of the heating element and/or a temperature of the vaporizing element.

In some embodiments, array 301 is coupled optionally through plate 311 to a heat sink 313. Optionally, the heat sink is coupled to a frame or housing of the array (not shown in this figure), for example to prevent a user from holding a heated component. In some embodiments, the heat sink comprises a water tank. In some embodiments, the heat sink comprises a thermoelectric chiller. A thermostat may be connected to the heat sink to control a temperature.

In some embodiments, array 301 and/or power source 307 are connected to a control unit 315. Control unit 315 is connected, in some embodiments, to a second power source 317. Optionally, a single power source is used for supplying power to heating element 303 and to control unit 315.

The following are some non-limiting examples of parameters which can be automatically and/or manually controlled through control unit 315. Some parameters may be selected by a user, while others may be automatically controlled by control unit 315. Some parameters may be set as a combination of both automatic and manual control. In some embodiments, control unit comprises a user interface. Some exemplary parameters are listed below:

A. Controlling a treatment temperature profile. Optionally, the temperature profile is adjusted by modifying the current conducted to heating element 303. In some embodiments, temperature sensor 309 provides an indication of the current temperature of the heating element, and the temperature profile is adjusted accordingly, affecting a temperature of vaporizing array 301. A typical response time of the control unit, for example to a detected change in temperature, may range between 1-10 seconds, such as 2 seconds, 4 seconds, 8 seconds, or intermediate, longer or shorter response time.

B. Controlling a movement profile of array 301. In some embodiment, for example as will be further shown, array 301 is coupled (either directly or through the heater 303) to a mechanism for allowing its movement to and from the treated tissue. In some embodiments, controlling a movement profile comprises controlling a distance in which the array is optionally elevated to between treatments. In some embodiments, controlling a movement profile comprises controlling an amount of force applied to advance array 301 into the tissue. In some embodiments, controlling a movement profile comprises controlling a velocity of the vaporizing array. In some embodiments, controlling a movement profile comprises controlling an acceleration rate of the vaporizing array. In some embodiments, controlling a movement profile comprises controlling a dwelling time of the tips of the vaporizing elements in the treated tissue. In some embodiments, controlling a movement profile comprises setting a number of repetitions. In some embodiments, controlling a movement profile comprises setting a time interval between repetitive treatments. In some embodiments, controlling a movement profile comprises controlling a motor or any other component, for example a component of a camshaft mechanism, which is utilized for moving the array.

C. Controlling the cooling of array 301 and/or a cooling of a frame or housing of the device and/or a cooling of other components of the system, by controlling a temperature of heat sink 313. Optionally, array 301 is maintained under a safe temperature by heat sink 313. In some embodiments, control unit 315 receives an indication from a thermocouple that is connected to heat sink 313, for example being a water tank. In some cases, for example to prevent overheating, if the thermocouple indicates a water temperature above a certain threshold, control unit 315 activates a thermostat to prevent heating element 303 from overheating.

D. Controlling a self-sterilization/self-cleaning profile. In some embodiments, as will be further described, a temperature of array 301 may be raised above, for example, 500 degrees Celsius, to cause removal of tissue particles and/or carbonized particles that adhered to the vaporizing elements following contact with the tissue, to produce a char-free array. Optionally, controlling includes setting a time (for example every 1-50 treatment pulses) for activating the self cleaning function and/or a duration of activation, for example ranging between 0.5-5 seconds.

In some embodiments, a system for example as described herein is configured as a hand-held device. Optionally, to provide a comfortable and safe use of the device, a temperature of the device housing is controlled, for example by positioning a temperature sensor adjacent to the external housing, to prevent it from overheating.

Optionally, a temperature sensor is positioned on and/or adjacent array 301 to detect a temperature of the array. Optionally, the array temperature is monitored, for example to prevent overheating of the vaporizing elements.

In some embodiments, at least a portion of array 301 is detachable, and can optionally be disposed, for example after a certain number of treatments such as 1, 3, 10, 50 or any other number of treatments. Optionally, array 301 is disposed of and replaced, for example in between patients.

Structure and Materials of a Vaporizing Element

Figure 4A:
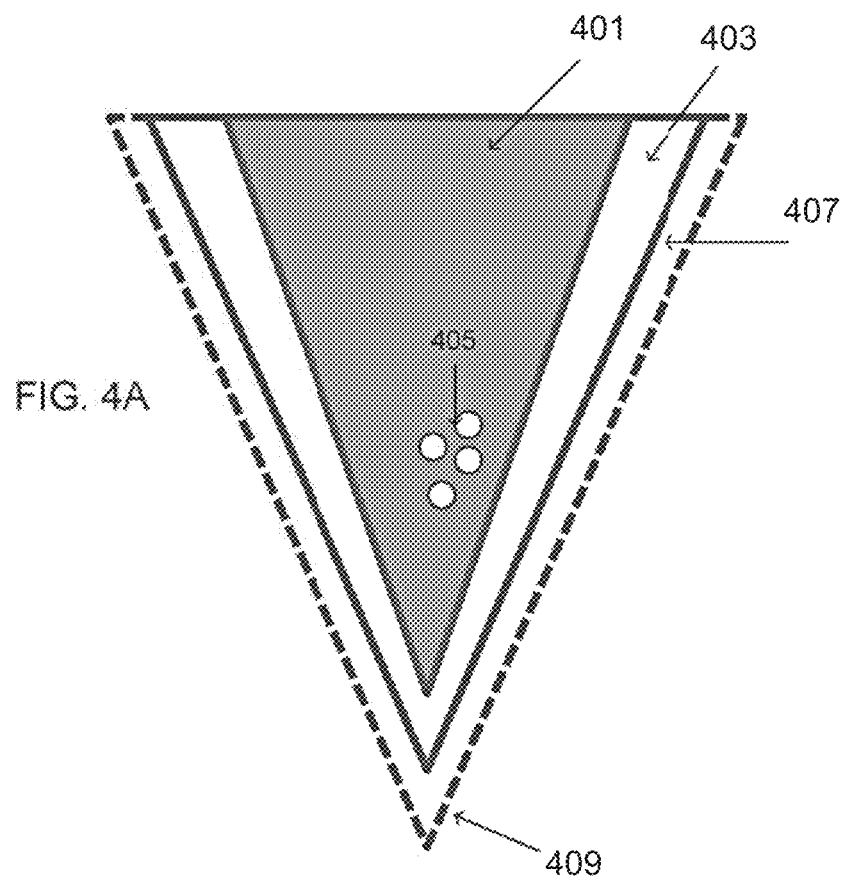
FIGS. 4A-B are schematic cross sections of a vaporizing element (4A) and a plate onto which the elements are mounted (4B), according to some embodiments of the invention.
Figure 4B:
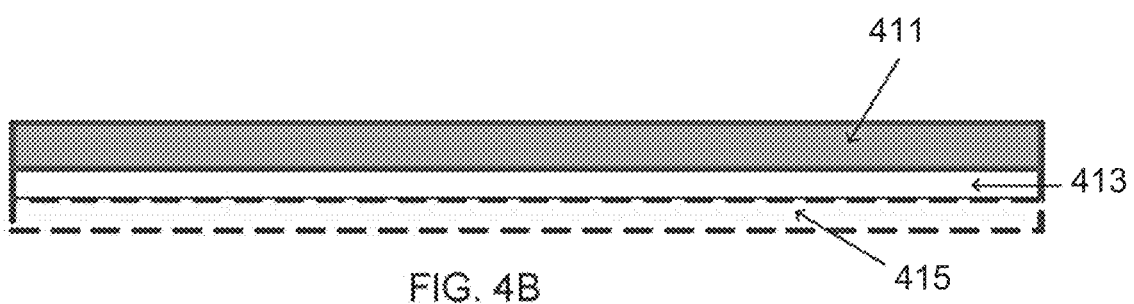

FIGS. 4A-B are schematic cross sections of a vaporizing element (4A) and a plate onto which the elements are mounted (4B), according to some embodiments of the invention.

In some embodiments, a vaporizing element (for example as shown in FIG. 4A) and/or a plate (for example as shown in FIG. 4B) onto which one or more vaporizing elements are mounted or are integrally connected to, comprise a multi layer structure, for example comprising 2, 3, 4, 6, or any other number of layers. Optionally, each layer comprises a different material. Optionally, each layer comprises a different thickness. In some embodiments, a material of the multi layer structure is selected to generate limited vaporization, for example as compared to an element formed only of copper. In some embodiments, a material is selected to reduce a damage region, for example surrounding the location of treated tissue. It is necessary that at least some of the materials from which the vaporizing element is constructed have a high thermal conductivity, for example having a thermal conduction coefficient higher than 80 Watts per degree Kelvin per meter. In some embodiments, a layer is adapted for maintaining a condition of an internal layer, for example a layer may reduce diffusion of particles from a layer underneath it. In some embodiments, at least one layer such as the external layer of the vaporizing element and/or the external layer of the plate that optionally have direct contact with tissue comprise a biocompatible material. In some embodiments, at least one layer such as the external layer has a relatively low IR emissivity level, and is capable of reducing IR radiation towards the tissue. In some embodiments, a layer such as an external comprises an electrically insulating material, such as Sapphire, so as not to produce an electrical contact with the tissue being vaporized. For example, a thin (such as 100 micron) layer of sapphire may efficiently conduct heat to tissue, while providing an electrical insulation.

Reference will be made now to FIGS. 4A-B, which show a conical vaporizing element comprising three layers. In some embodiments, a body 401 of a vaporizing element is made a material comprising a relatively high thermal conduction coefficient, such as copper. Other materials may include aluminum nitride, stainless steel, ceramics, glass, and/or combinations of them, depending on the type of application.

In some embodiments, body 401 is made of sintered copper, and/ or sintered stainless steel, and/or sintered aluminum nitride (ALN). Optionally, a sintered material comprises less burrs, for example as opposed to machined material.

Optionally, a surface of the sintered material is smooth enough so that it can be uniformly coated, for example by a different material.

In some embodiments, body 401 is coated by second layer 403, for example made of silver. Optionally, a thickness of layer 403 ranges between 5-20 μm. The inventors have shown that silver layer 403 is capable of reducing diffusion of copper ions 405 in body 401, a commonly known phenomena which may be observed in copper heated to high temperatures, for example heated to 300 degrees Celsius. A potential advantage of reducing and/or eliminating the diffusion of copper includes maintaining biocompatibility of the heated material. In some embodiments, layer 403 is coated by an additional layer 407. In some embodiments, layer 407 comprises a biocompatible material, as it comes in direct contact with tissue. In some embodiments, layer 407 comprises a material having relatively low IR emissivity, and may reduce IR radiation towards the treated tissue. In some embodiments, layer 407 is made of gold and/or rhodium. Additionally or alternatively, layer 407 comprises carbon, diamond, graphene, palladium, titanium nitride, titanium, stainless steel and/or other materials. Optionally, a thickness of layer 407 ranges between 0.5-10 μm.

Optionally, layer 407 acts as a barrier to diffused silver ions, preventing the released ions from reaching the tissue.

In some embodiments, layer 403 and/or layer 407 comprise a material that is optionally less heat conductive than a material from which body 401 is made of, for example layer 403 and/or layer 407 can be made of stainless steel or titanium.

In some embodiments, a thickness ratio between the layers changes along various portions of the vaporizing element, for example tip 409 at a distal end of the vaporizing element may be structured such that body 401 extends to the end of the tip, and a thickness of layers 403 and/or 407 is reduced. In some embodiments, layers such as coating layers 403 and/or 407 are not evenly distributed, and are thicker along some portions and thinner in others.

In some embodiments, the layered structure is manufactured using electroplating technologies. In some embodiments, the layers are deposited using chemical vapor deposition techniques, and/or by sputtering. For example, a layer of titanium nitride can be applied by sputtering.

FIG. 4B shows an exemplary layer structure of a plate, according to some embodiments of the invention. In some embodiments, a layer structure of the plate is similar to the layer structure of a vaporizing element. Alternatively, the plate comprises a different layer structure than the vaporizing element. In some embodiments, the plate comprises a single layer, for example made of copper, ceramics and/or stainless steel.

In some embodiments, a total thickness of the plate is thick enough to prevent bending of the array, and on the other hand, thin enough to allow a rapid transfer of heat from the heating element to the vaporizing elements. Optionally, a total thickness of the plate ranges between 0.5-10 mm, for example 1 mm, 3 mm, 6 mm.

As shown in this example, the plate comprises three layers, similarly to the vaporizing element in FIG. 4A: A copper layer 411, optionally facing a surface of a heating element, a middle layer 413, for example made of silver, and an external layer 415, for example made of gold and/or rhodium, facing towards the tissue.

In some embodiments, only some portions of the plate, for example exposed surfaces in between vaporizing elements, are coated by a biocompatible material and/or an IR radiation reducing material such as gold.

Figure 5:
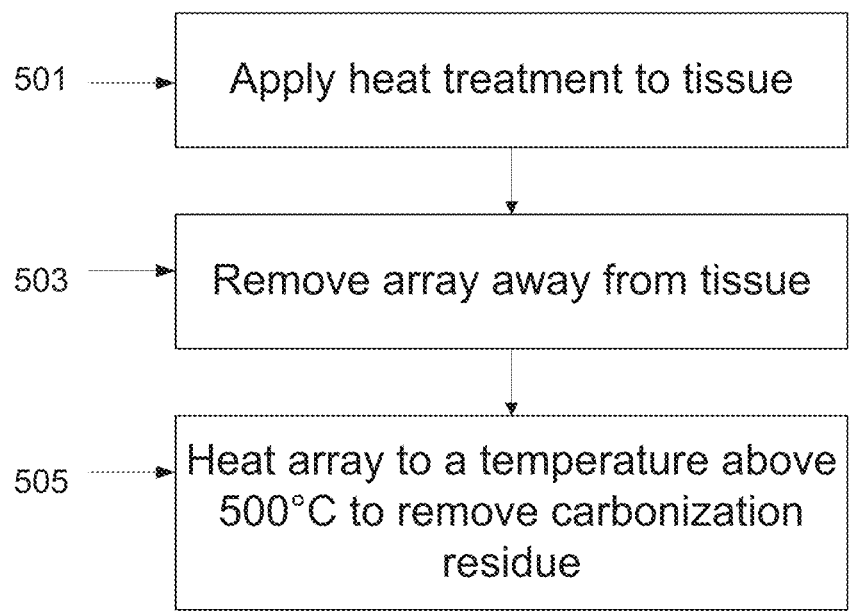
FIG. 5 is a flowchart of a method for self sterilization of an array comprising vaporizing elements, according to some embodiments of the invention.

In some embodiments, the vaporizing elements and/or plate are manufactured using a metal injection molding process, in which powdered metal is mixed with binder material to form a 'feedstock' mix, which is then injected to a hollow mold, and sintered to produce the final product. Optionally, conditions such as a sintering temperature, the type of materials used, the mold dimensions are selected such that the end product is accurately formed according to preselected dimensions.

A Method for Self Sterilization of an Array of Vaporizing Elements FIG. 5 is a flowchart of a method for self sterilization of an array comprising vaporizing elements, according to some embodiments of the invention.

In some embodiments, as the multi layer structure withstands high temperatures, the array is adapted for self cleaning and/or self sterilizing. In some embodiments, self cleaning maintains a char free array. In some embodiments, self sterilization is required to clear an array from tissue particles and/or carbonized particles that may have adhered to the array during treatment.

In some embodiments, the method includes applying vaporization treatment to the tissue (501), for example skin tissue. Optionally, repetitive treatment is applied, for example comprising 2, 5, 10, 20, 50 or any intermediate or higher repetitions. Following treatment, for example once a desired vaporization depth was achieved, the array is moved away from the treated tissue (503).

In some embodiments, to clean and/or sterilize the array, the array is heated to a temperature over approximately 500 degrees Celsius (505). In one example, the array is heated to 550 degrees Celsius for time period ranging between 0.5-5 seconds. Optionally, heating to such a high temperature causes oxidation, which transforms carbon residue such as tissue particles and/or carbonized particles that exist on the array into $CO_2$ vapors.

The inventors have conducted experiments to prove the cleaning effectiveness of heating to a temperature over 500 degrees. They applied treatment to tissue at 380-400 degrees Celsius, which gradually caused a thin carbonization layer to form on a surface of some vaporizing elements and on a portion of the plate. After removal of the array from the tissue, the array was heated to 550 degrees Celsius for a time period ranging between 1-3 seconds, after which all carbonization residues were discarded.

In some embodiments, sterilization and/or cleaning is applied after a certain number of treating pulses, for example 1-50 treating pulses. In some embodiments, sterilization is applied according to accumulating operation time, for example every 10 seconds, 40 seconds, 2 minutes, 5 minutes, 20 minutes, 60 minutes, or intermediate, higher or smaller durations of operation.

In some embodiments, one or more vaporizing elements and/or the array of vaporizing elements are removed from the device (e.g. a handheld device), for example following treatment, and are replaced by new vaporizing elements or a new array of vaporizing elements. Optionally, replacing is performed robotically.

Optionally, replacing is controlled by a controller of the device.

A Method for Repetitive Vaporization of Tissue

Figure 6:
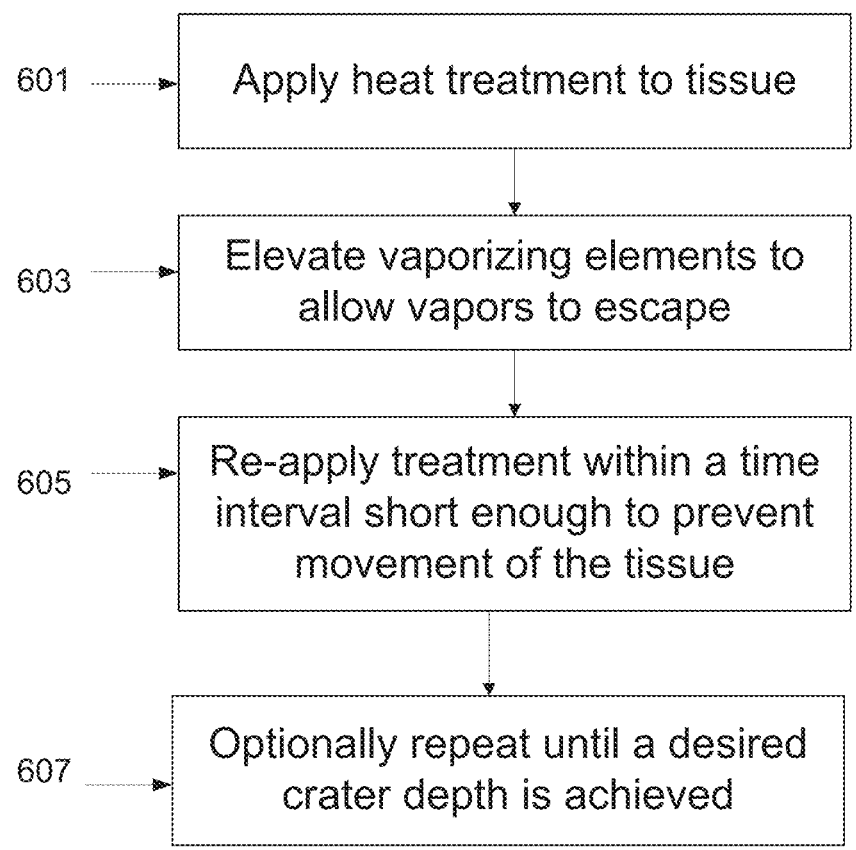
FIG. 6 is a flowchart of a method for applying repetitive treatment pulses, according to some embodiments of the invention.

FIG. 6 is a flowchart of a method for applying repetitive treatment pulses, according to some embodiments of the invention.

In some embodiments, vaporizing the tissue includes applying repetitive treatment pulses, for example for producing a deeper crater in the tissue.

In some embodiments, a first treatment pulse is applied (601). In some embodiments, following the treatment pulse, the vaporizing elements are elevated from the tissue (603), for example elevated so that their distal tips are positioned above a surface of the tissue. Optionally, vapors such as $CO_2$ vapors may be trapped between a distal end of a vaporizing element and the crater, and by elevating the vaporizing element at least a portion of the vapors, such as 50%, 70%, 90% of the formed vapors are allowed to escape. A potential advantage of releasing vapors may include vaporizing deeper craters.

In some embodiments, a ventilator is coupled to the device to accelerate the clearing of the vapors. Additionally or alternatively, a pump or other device capable of providing suction is coupled to the device to accelerate the clearing of vapors.

In some embodiments, a second treatment pulse is applied (605). Optionally, the second treatment is applied within a time interval short enough so that tissue movement is prevented. Optionally, this allows for repositioning a vaporizing element in a similar location with respect to the crater walls as it was positioned before, optionally reducing collateral damage and/or the formation of craters with poorly defined borders.

In some embodiments, repetitive treatment pulses are applied (706), such as 3 pulses, 5, pulses, 10 pulses, 50 pulses. In one example, 3 treatment pulses are applied with a 50 msec time interval between them. In some embodiments, 1-15 treatment pulses are applied within a 1 second time period. Optionally, a time interval between two treatment pulses is shorter than 200 msec.

Optionally, by applying repetitive treatment pulses, deeper tissue layers are vaporized, forming deeper craters.

Repetitive treatment for formation of deeper craters may be useful, for example, in cases where a thick epidermis layer exists, and attaining a papillary dermis layer is desired.

Figure 7A:
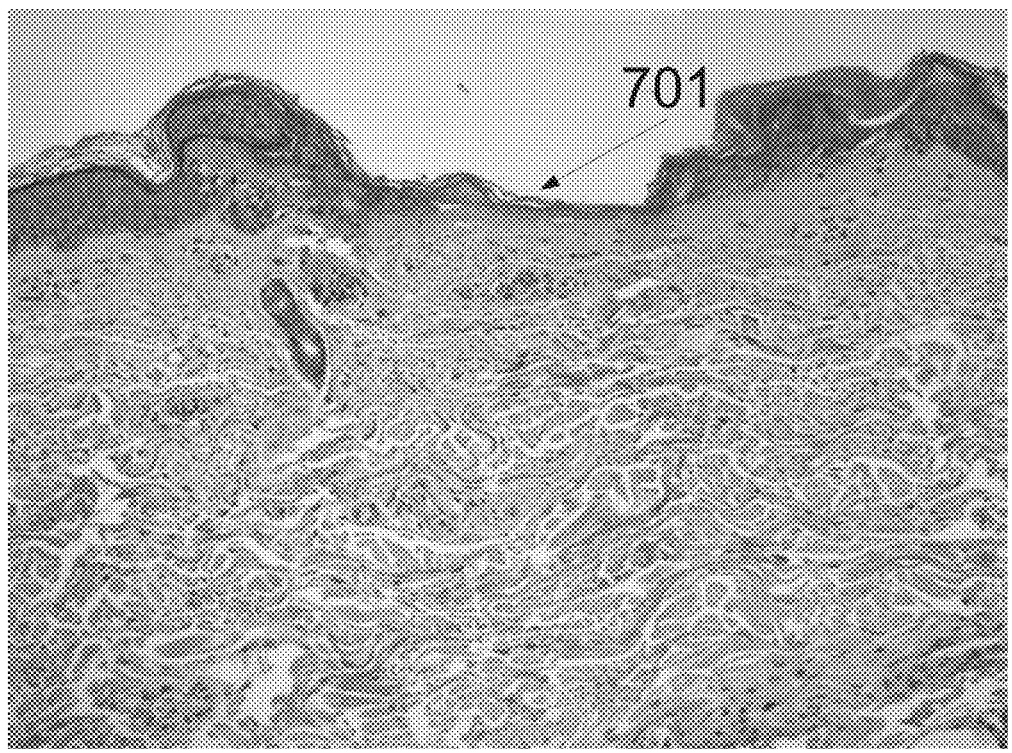
FIGS. 7A-B are histological results of tissue vaporization, according to some embodiments of the invention.
Figure 7B:
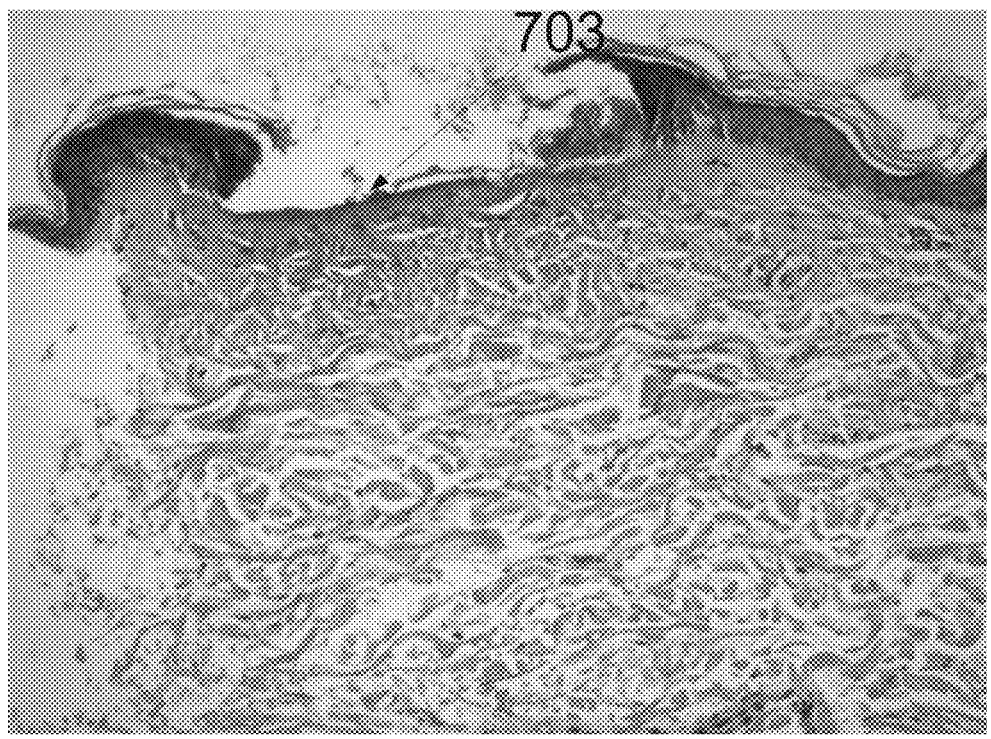

FIGS. 7A-B are histological results of tissue vaporization, according to some embodiments of the invention.

The histological results shown in both examples were obtained by using an array of 9×9 pyramidal shaped vaporizing elements, each pyramid having a height of 1.25 mm, and a width of an edge of the square base of 1.25 mm. Each element comprised a copper body coated by a layer of nickel and/or gold, having a thickness of 10 μm.

In FIG. 7A, a single treatment pulse was applied at 400 degrees Celsius to the tissue. The image shows a single crater 701, formed by a single vaporizing element.

Applying a single treatment pulse resulted in forming the relatively superficial crater in the papillary dermis, which was 100 μm deep.

In FIG. 7B, a triple treatment pulse was applied at 400 degrees Celsius to the tissue. A time interval between the repetitive treatment pulses was 50 msec. As can be observed, a deeper (having a depth of approximately 150 micron) damaged zone 703 was formed in the tissue, having clearly defined walls.

An Exemplary Movement Profile of an Array of Vaporizing Elements

Figure 8A:
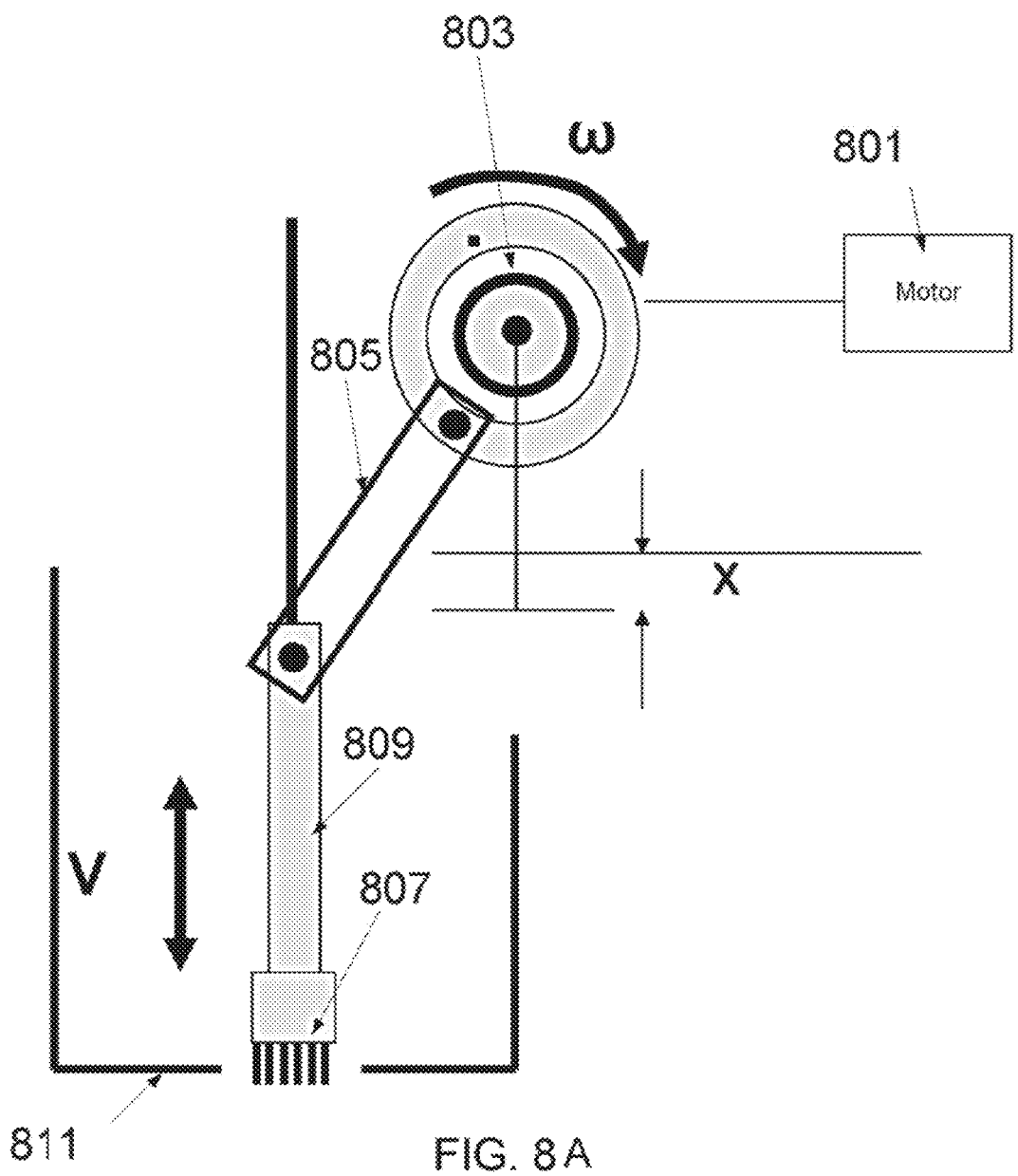
FIGS. 8A-B are a schematic diagram showing a cyclic movement profile implementation utilizing a camshaft mechanism, and an exemplary movement profile, according to some embodiments of the invention.

FIG. 8A shows a cyclic movement profile implementation, for example utilizing a camshaft mechanism, according to some embodiments of the invention.

In some embodiments, operating of an array of vaporizing elements includes producing a cyclic movement profile of the array. In some embodiments, the absolute acceleration rate of the vaporizing elements increases as the elements advance toward the tissue. Optionally, the maximal absolute acceleration rate is achieved at the tissue contact point. Optionally, once the element contacts the tissue, the direction of velocity reverses, and the element is retracted from the tissue. Optionally, the reversal of direction occurs within a relatively short duration, for example ranging between 10 microsec and 100 millisec from a time of contact with the tissue. In some embodiments, the absolute acceleration rate increases along at least a portion of the pathway of the elements towards the tissue, for example along 20%, 30%, 50%, 70% or intermediate, larger, or smaller portions of the pathway. Optionally, the absolute acceleration rate increases at the initial advancement of the array towards the tissue.

Additionally or alternatively, the absolute acceleration rate increases as the array moves closer to the tissue.

In some embodiments, the absolute acceleration rate is set such as to achieve a short dwelling time of the vaporizing elements within the tissue, for example 100 μsec.

It is possible that by shortening a dwell time in tissue, collateral damage is reduced. It should be noted that in some cases, a longer dwell time such as 1-100 msec is desirable, for example in cases where delayed healing is advantageous. Additional exemplary dwelling times of vaporizing elements are 1 msec, 6 msec, 14 msec, 18 msec and 25 msec. The selection of dwelling time duration also depends on the vaporizing tip material. For example, a copper tip may require 6 msec for vaporization of a 100 micron deep crater, an ALN tip may require 14 msec and a stainless steel tip may require 18 or 25 millisec.

Exemplary absolute acceleration rates range between, for example, $0-2\times10^5$ cm/sec$^2$, for example between $2\times10^3-2\times10^5$ cm/sec$^2$.

Figure 8B:
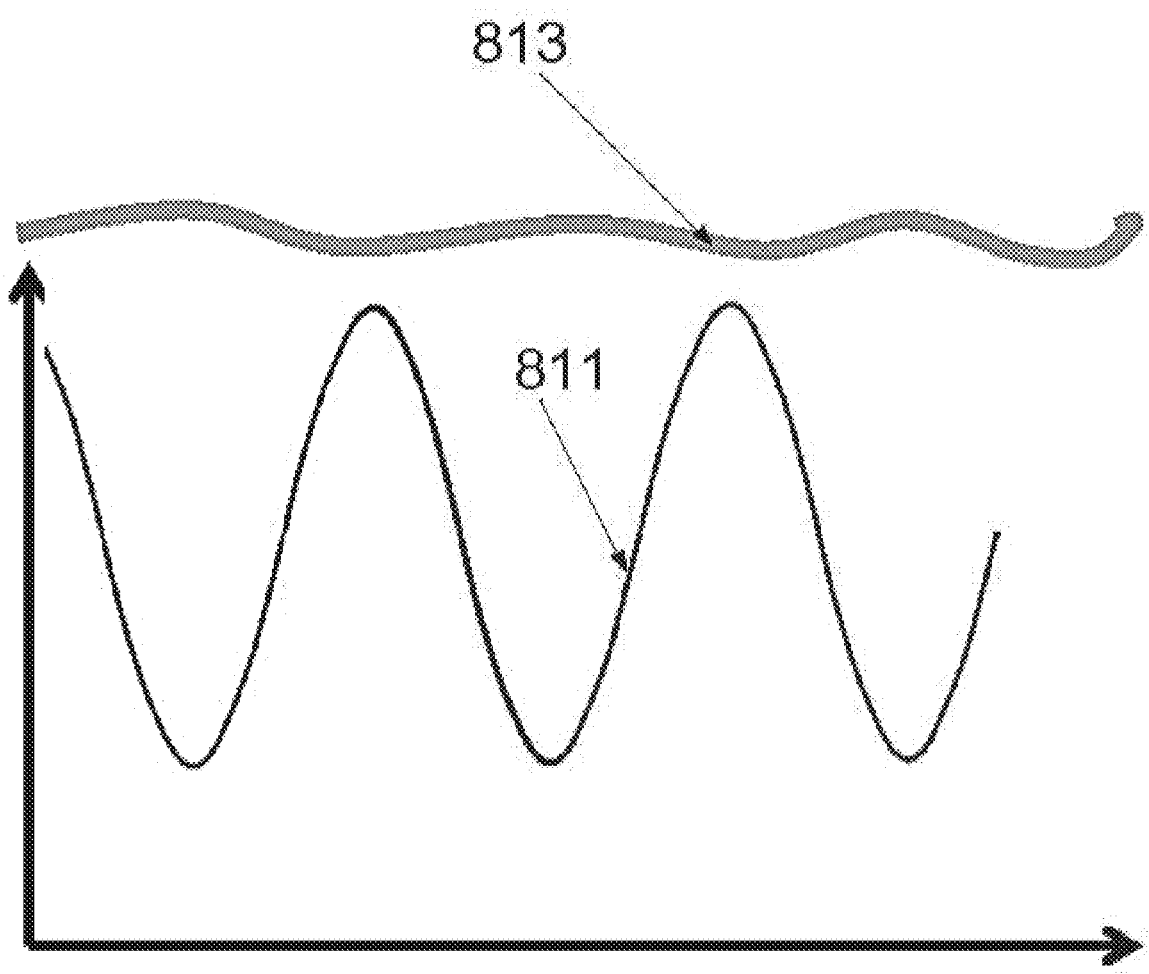

In some embodiments, a camshaft based mechanism, for example as shown in FIGS. 8A-B, is utilized for generating a cyclic movement profile of an array, transforming angular velocity into linear velocity of the array.

In some embodiments, a motor 801 operates a rotating wheel 803, for example spinning the wheel at an angular velocity w. In some embodiments, motor 801 is a DC motor. Motor 801 can be a stepper motor, an axial rotor motor, or any other type of motor suitable for causing a rotation of wheel 803.

In some embodiments, wheel 803 is attached to a lever 805, which translates a circular motion of wheel 803 to a linear motion of the array of vaporizing elements 807. In some embodiments, a shaft 809 connects between lever 805 and array 807.

During operation, rotation of wheel 803 causes lever 805 to lift and lower shaft 809 by a distance, which ranges between, for example, 3-25 mm, for example 10-15 mm, at a linear velocity V, which changes as a function of the array position.

In some embodiments, for example to provide precise control over the oscillations of the array of vaporizing elements, specifically of the distal tips of the vaporizing elements, marked by distance X, measuring means such as a micrometer can be used. Optionally, the micrometer is attached to wheel 803. In some embodiments, distance X ranges between 50-2000 μm.

In some embodiments, distance X affects the protrusion of the vaporizing elements of array 807 from a distal end of a housing of the treatment device 811, for pushing against the tissue during treatment. The extent of the protrusion may range, for example, between 0-2 mm, such as 0.3 mm, 0.5 mm, 1 mm, 1.8 mm. In some cases, for example when tissue such as skin tissue is pushed up while placing and pressing the array against the skin, at least a portion of the skin may bulge in between the vaporizing elements. In such a case, the extent of protrusion can be referred to as a negative distance, for example −1 mm, thus compensating for the skin bulging.

In some embodiments, linear velocity V of the array ranges between 0-150 cm/sec, such as 70-100 cm/ sec, 10-20 cm/sec, 30-50 cm/sec.

In some embodiments, an encoder such as an, optocoupler, Hall magnetic sensor, or any other circuit, is incorporated into motor 801, for generating an indication of a current position of array 807, and/or information about the wheel velocity, and/or information about the array velocity.

In some embodiments, an indication is transferred to a control unit, for example as explained hereinabove. Optionally, the control unit activates the camshaft mechanism, for example according to parameters selected by a user, and/or parameters selected automatically by the control unit. For example, a user can select parameters such as the velocity of array, the advancement and retraction distance, a dwelling time of the array in the tissue, a number of repetitions, a penetration depth of the vaporizing elements in the tissue, and/or any other parameters.

In some embodiments, array 807 is attached to a spring. Optionally, a stiffness of the spring and/or an oscillation distance of the spring affect an acceleration rate of the array towards the tissue, and/or a dwelling time of the vaporizing elements within the tis sue.

In some embodiments, the array assembly, for example operated by the camshaft mechanism and/or the spring, comprises a sensor adapted for detecting a current position of the array, such as an optocoupler.

In some embodiments, the array assembly comprises a sensor for measuring a dwelling duration of the vaporizing elements within the tissue, for example by measuring electrical conductivity of the tissue using, for example, a resistor and a low voltage power supply such as a battery. Optionally, the power supply is low enough to maintain the current level under a level set by clinical standards, for example 100 microampere.

In some embodiments, a safety mechanism is configured for receiving an input from a sensor, for example as described herein, and elevating the array and/or pushing the tissue ahead away from the array if the dwelling duration is longer than permitted and/or if a current position of the array indicates malfunction. Optionally, an additional spring is provided for elevating the device in case of malfunction.

Optionally, a push-down frame is provided for pushing the tissue away from the array in case of malfunction.

FIG. 8B shows an exemplary graph indicating a cyclic movement profile of a vaporizing array, according to some embodiments of the invention. The graph shows an absolute acceleration rate 811 of the vaporizing array as a function of location with respect to the treated tissue 813. In some embodiments, as the vaporizing array advances toward the tissue, the absolute acceleration rate increases, reaching a maximal absolute value upon contact with tissue 813. Optionally, for example upon reaching the desired depth in tissue, the direction of the vaporizing array is reversed and the vaporizing array is elevated from the tissue. Optionally, for example when repetitive pulses are applied, as shown in this figure, the direction of the array is reversed again so that it advances toward the tissue and so forth. In some embodiments, the movement profile of the vaporizing array is determined such as to shorten a dwelling duration of the elements within in the tissue.

A Dual System for Delivering RF Energy and/or Vaporizing Tissue

Figure 9:
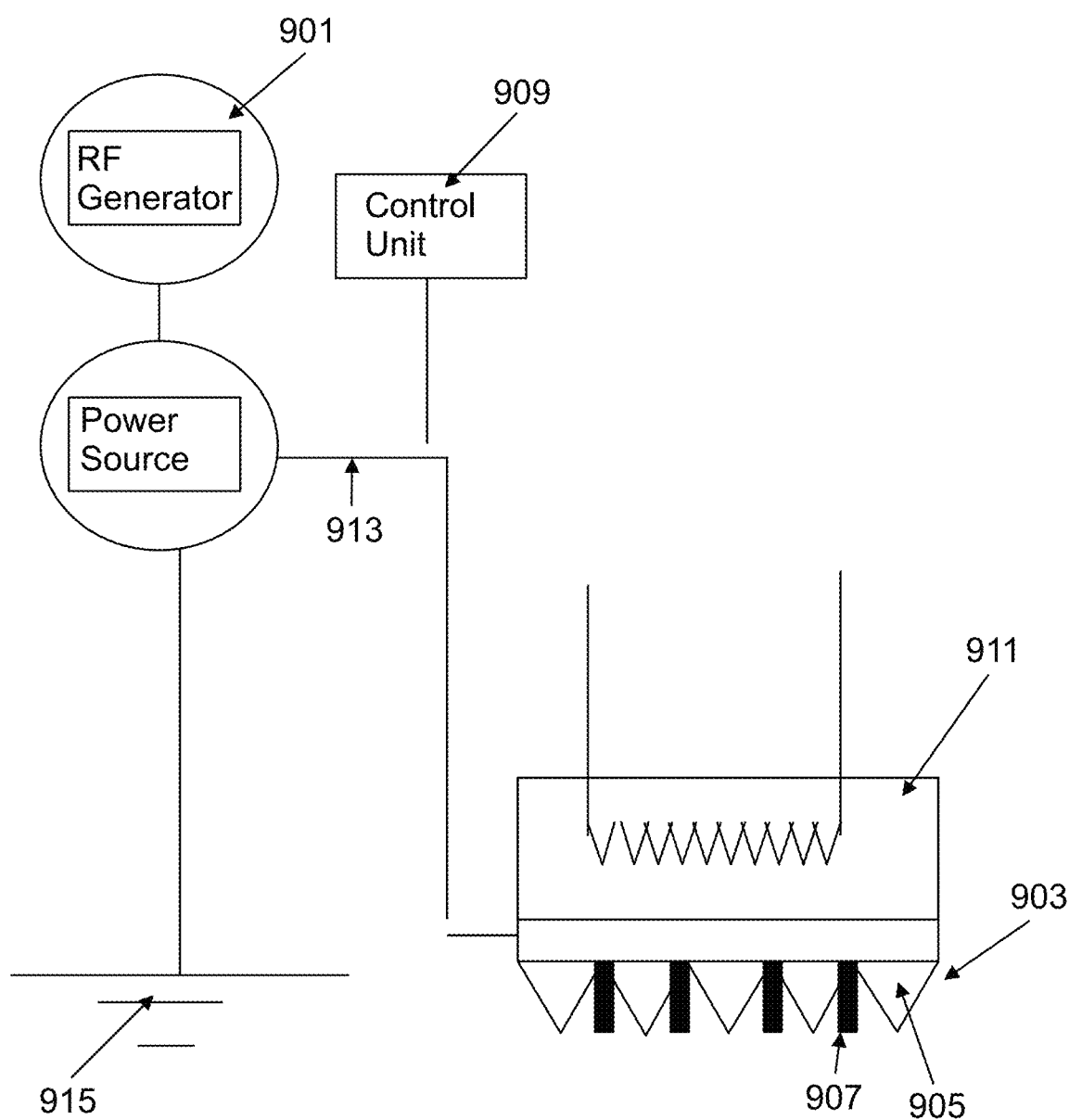
FIG. 9 is a block diagram of a system for tissue vaporization comprising an RF generator, according to some embodiments of the invention.

FIG. 9 is a block diagram of a system for tissue vaporization comprising an RF generator, according to some embodiments of the invention.

In some embodiments, an RF generator 901 is incorporated in a system, for providing a dual functioning device adapted for a thermal activation mode and an RF energy activation mode.

In some embodiments, array 903 comprises a combination of vaporizing elements 905, and RF electrodes 907.

Alternatively, vaporizing elements 905 are adapted for transmitting RF energy to the tissue. Optionally, vaporizing elements made of metal such as copper and/or stainless steel are suitable for transmitting the RF.

Alternatively, array 903 comprises only RF electrodes. In some embodiments, a conduit 913 such as an RF antennae is used for transferring RF energy from generator 901 towards the tissue. In some embodiments, the array comprises thermally conductive elements, which are not necessarily configured for vaporizing the tissue.

In some embodiments, a control unit 909 is configured for switching between a thermal heating mode and an RF energy transmitting mode, for example activated by an electrical switch which may be operated by a user. If an RF energy transmitting mode is selected, RF energy generated by RF generator 901 is transmitted by array 903 into the tissue to cause ablation. If a thermal mode is selected, the vaporizing elements 905 are heated by a heating element 911 to vaporize the tissue. In some embodiments, both modes are activated simultaneously.

A system comprising an RF generator may be particularly useful in fractional skin resurfacing applications.

In some embodiments, the system comprising an RF generator is operated at a cyclic movement profile, for example utilizing a camshaft mechanism as described herein.

A Foil for Vaporizing Tissue

Figure 10:
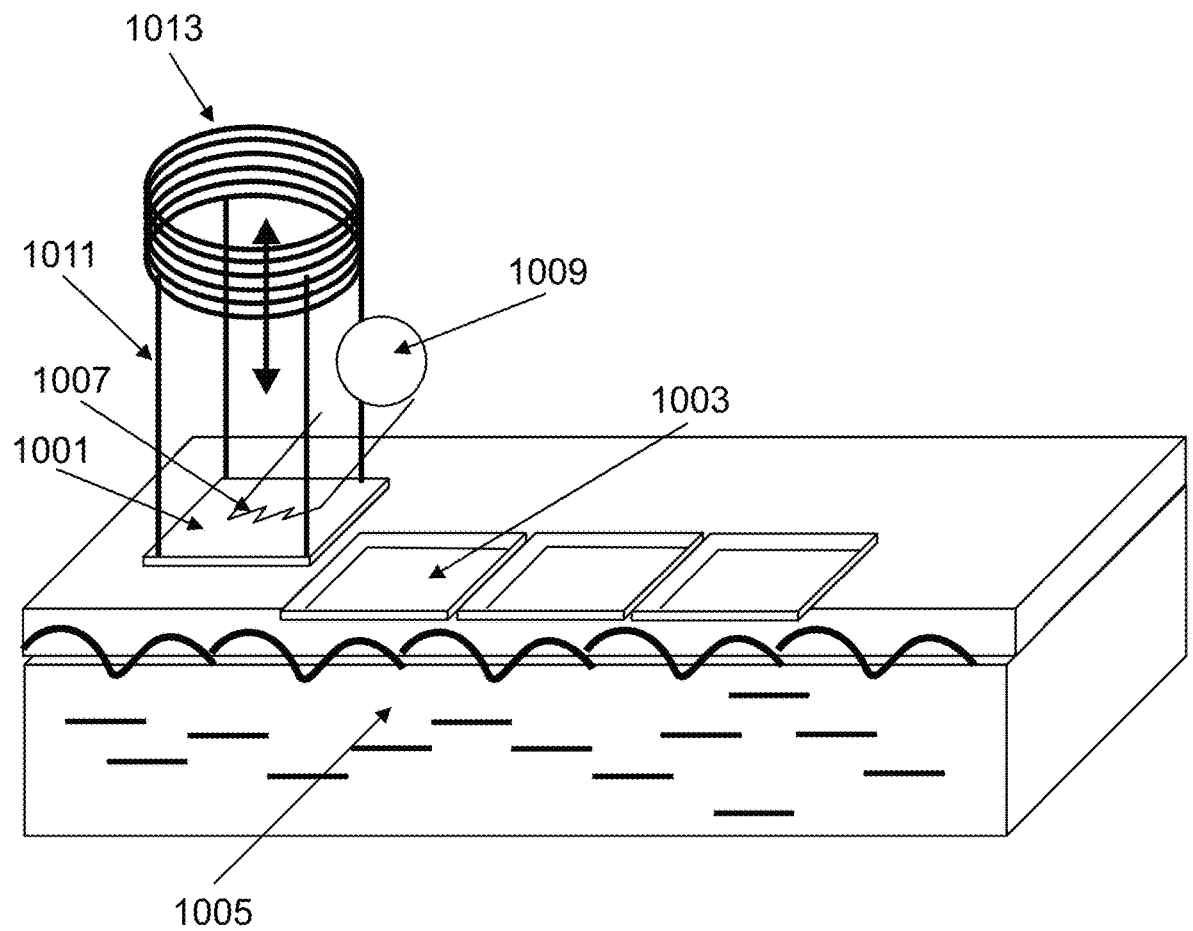
FIG. 10 is an illustration of a foil for vaporizing tissue, according to some embodiments of the invention.

FIG. 10 illustrates a foil for vaporizing tissue, according to some embodiments of the invention.

In some embodiments, for example as described hereinabove, a size of a crosswise surface of a vaporizing element contacting the tissue is relatively small, for example if the element is shaped to penetrate to a certain depth in the tissue, a length of the element is significant. In some embodiments, a surface of the vaporizing element contacting the tissue is relatively large, for example if the element is shaped as a foil, such as a planar foil.

In some embodiments, a vaporizing element is shaped in a planar configuration having a small thickness, such as a foil 1001, for vaporizing a superficial crater 1003 adjacent a surface of tissue 1005. A depth of crater 1003 may range between, for example, 0-50 μm.

In some embodiments, foil 1001 is heated by a wire 1007, for example a copper wire. Optionally, wire 1007 is mounted on a surface of foil 1001 facing away from the tissue. Optionally, wire 1007 is embedded within foil 1001. In some embodiments, wire 1007 is coated by an electrically insulating material. The ends of wire 1007 are connected directly or indirectly (for example through an additional wire) to a power source. In some embodiments, the power source is a low voltage power source, such as a 0.5-9 V battery 1009.

In some embodiments, a frame 1011 is provided for holding foil 1001.

Optionally, since foil 1001 is relatively light, for example weighing less than 1 gram, frame 1011 ensures full contact between the surface of foil 1001 and the tissue. In some embodiments, foil 1001 is held at a slightly concave position, so that frame 1011 does not contact the tissue.

In some embodiments, frame 1011 is adapted for heating foil 1001, for example by the frame being coupled to a heating element.

In some embodiments, frame 1011 is attached to a spring 1013 for advancing and retracting foil 1001. Additionally or alternatively, a coil and magnet assembly are utilized for moving foil 1001. In some embodiments, spring 1013 is configured performing a single oscillation upon activation.

In some embodiments, foil 1001 comprises an electrically insulating coating, for example glass or Aluminum Oxide coating. In some embodiments, the coating comprises chrome nitride, and/or aluminum nitride.

In some embodiments, a safety mechanism is provided. Once foil 1001 contacts tissue 1005 and thermal energy is depleted to vaporize the tissue, a contact between the power source such as battery 1009 and heating wire 1007 is disconnected. Optionally, once foil 1001 is retracted from the tissue, the contact is reestablished and wire 1007 is heated again. Disconnection and/or reconnection of the power source are performed mechanically, and/or electrically, for example using a transistor.

In some embodiments, grounding 915 is provided.

In some embodiments, a surface area of foil 1001 ranges between 1 mm^2-5 cm^2.

In some embodiments, foil 1001 is shaped as a thin strip, for example having a width of 100 μm. Optionally, in that case, foil 1001 functions as a heating wire, and may conduct current. To eliminate current conductance into the tissue, foil 1001 is coated by an electrically insulating material. Additionally or alternatively, a relatively low voltage power source is used.

In some embodiments, foil 1001 is made of stainless steel or titanium.

Optionally, foil 1001 is manufactured and/or applied to the vaporizing element using electroplating and/or electropolishing techniques. In some embodiments, foil 1001 is made of glass.

Foil 1001 may be particularly useful in skin treatments such as exfoliation and/or micro-dermabrasion, often performed by cosmeticians. The foil can be used for treating thin surface layers of skin tissue, for example around the eyes, neck, and hands.

The following is an exemplary parameter calculation of an application comprising a use of a thin foil for treating a surface layer of skin.

In this example, a foil made of glass (with a heat conductance coefficient of ~1 W/mdeg C.) is used. The thickness of the foil is 1 mm, the volume is 0.1 cm^3, and the weight (M) is 0.3 grams.

A spring with a constant k=100 N/m and an oscillation amplitude of X=1 cm is used. A duration of a single oscillation is T~10 msec.

The foil and spring assembly are configured for pushing the skin to a distance of Y=2 mm in a single oscillation.

The dwelling time of the foil within the tissue, using the described assembly, can be calculated by the following equation: $t = 2 * \sqrt{2MY/kX}$, for example in this case t=2 msec.

In the above described conditions, the depth of a crater formed in the tissue is approximately 15 μm. (A depth of the outermost layer of the skin, the stratum corneum, is estimated at 15 μm.)

To calculate a thickness of a layer (Z) in which heat is dissipated from a location in the glass foil heated to the highest temperature to a location of the tissue surface, the following equation may be applied: $Z = \sqrt{Kt/\rho C}$ where:

K is the thermal conductivity of glass, for example ~10^-2 W/cmDeg C.

P the density of the glass foil, for example 3 gr/cm^3.

C is the heat capacity of the glass foil, for example ~0.8 J/gr*deg C.

For a dwelling time of the glass foil within the tissue of 2 msec, as shown above, the calculated thickness of the heat dissipation layer is Z~30 μm.

The amount of thermal energy stored in a 30 μm of glass, at a temperature of 500 degrees, obtained by multiplying the heat capacity (C) by the temperature, is 4 J.

Therefore, is it shown that during a 2 msec dwelling period, thermal energy of 4 J can be depleted by the foil to the tissue, in order to vaporize the tissue. Since the energy required to vaporize water is ~3000 J/cm^3, an energy of 4 J is capable of vaporizing a volume of 1.3*10^-3 cm, therefore a crater having a depth of 13 μm can be formed, (assuming square dimensions of the crater and the vaporizing foil).

Figure 11:
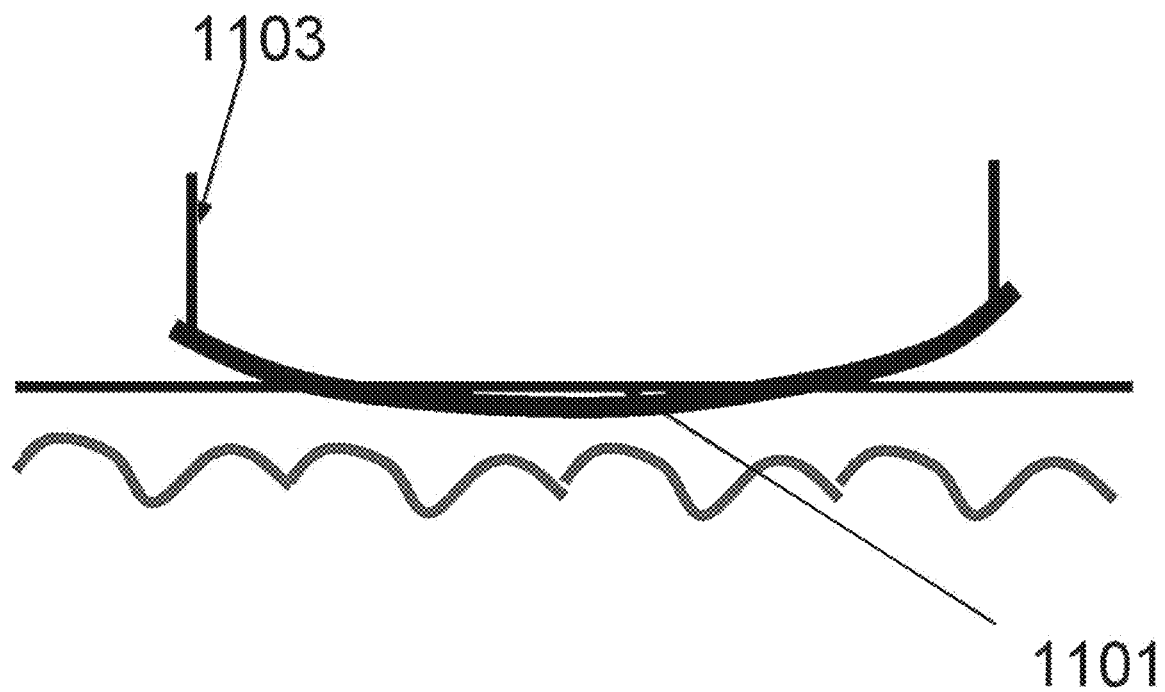
FIG. 11 shows an exemplary configuration of a planar vaporizing element being held by a frame, according to some embodiments of the invention.

FIG. 11 shows an exemplary configuration of a planar vaporizing element 1101, being held by a frame 1103 (only a portion of the frame is shown), according to some embodiments of the invention.

In some embodiments, foil 1101 is attached to frame 1103 in a way that a concave contour of the foil is formed. During operation, it is possible that the rods of frame 1103 absorb at least some of the heat from foil 1101. Over time, the rods of frame 1103 may heat to a higher temperature than the rest of foil 1101, and possibly cause overheating at the edges of foil 1101. To prevent overheating of the crater borders, the presented configuration can be utilized to lift the edges of foil 1101 away from the tissue during treatment.

A Hand Held Tissue Vaporization Device

Figure 12:
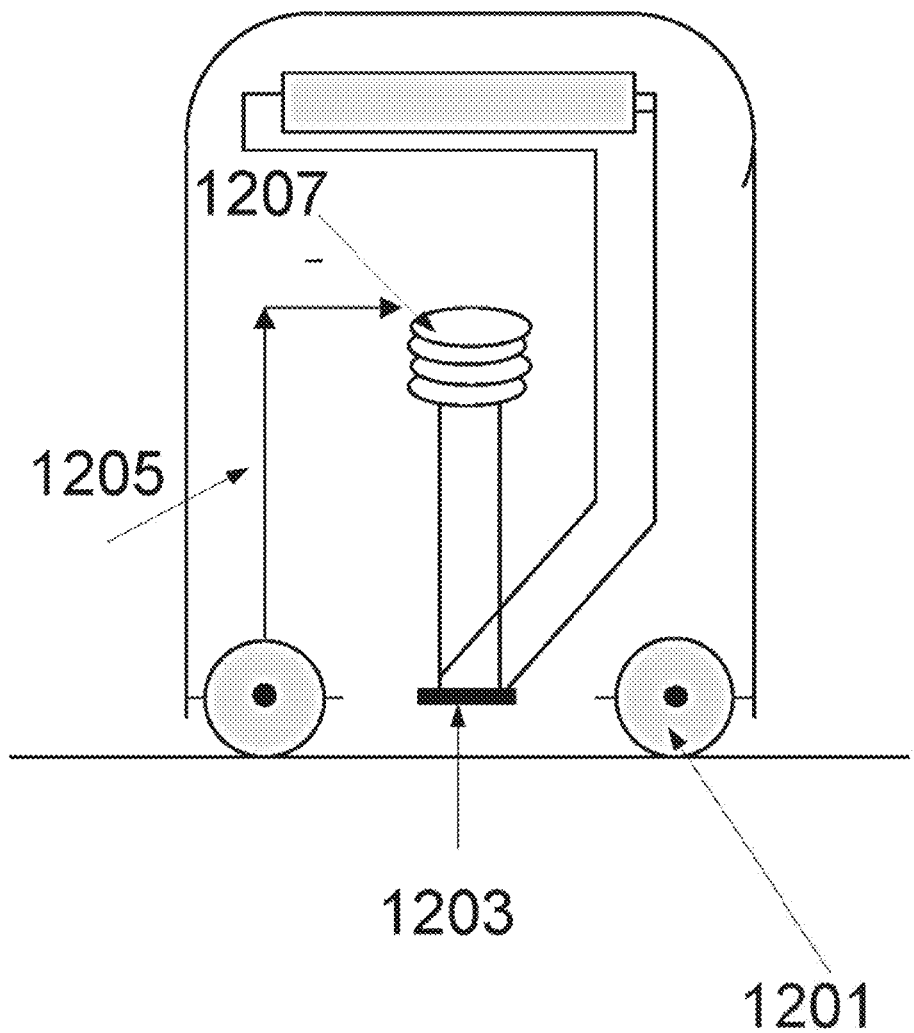
FIG. 12 is a drawing of a hand held tissue vaporization device, according to some embodiments of the invention.

FIG. 12 is a drawing of a hand held tissue vaporization device, according to some embodiments of the invention.

In some embodiments, an assembly of one or more vaporizing foils for example as described above in FIG. 10 is incorporated within a hand held device. In some embodiments, a distal portion of the hand held device (facing the tissue), comprises one or more wheels 1201. Optionally, a user slides the device on a surface of the tissue, for example the skin. A diameter of wheel 1201 can be configured to advance a vaporizing foil 1203 a certain distance, for example 1 mm, 5 mm, 1 cm, 2 cm. In some embodiments, a lever and/or cable 1205 is provided so that rotation of wheels 1201 applies force onto spring 1207, which in turn pushes foil 1203 towards the tissue. Optionally, lever 1205 retracts the spring so that in between treatments, foil 1203 is positioned away from the tissue.

A potential advantage of using a device comprising an advancement mechanism includes treating large surface area, such as facial skin.

Figure 13:
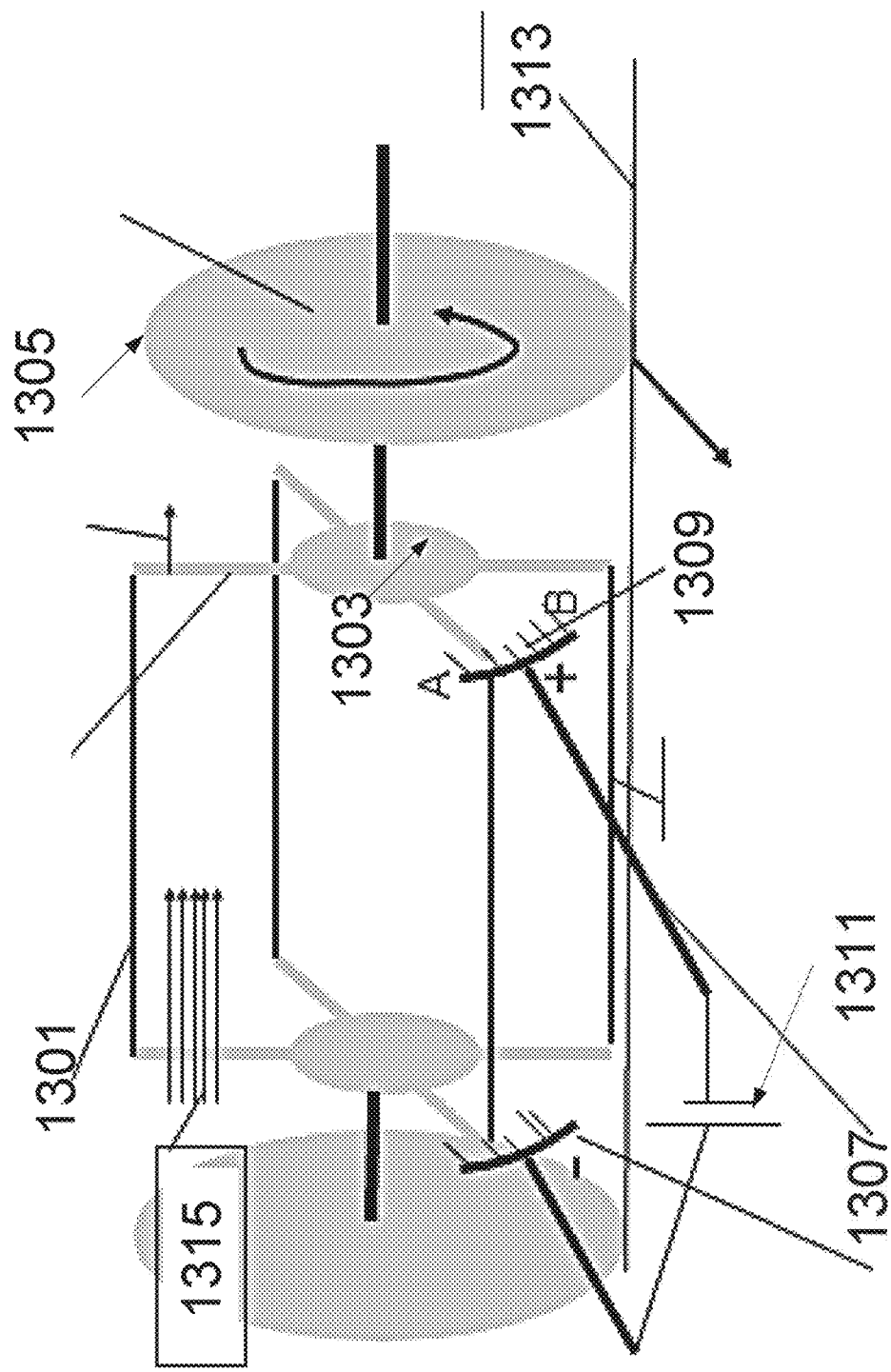
FIG. 13 is a drawing of a device for vaporizing craters in tissue, according to some embodiments of the invention.

FIG. 13 shows a device for vaporizing craters in tissue, according to some embodiments of the invention.

FIG. 13 illustrates a device configured for rolling over a surface of the tissue. In some embodiments, the device comprises at least one wire 1301 for vaporizing a narrow, elongated crater. In some embodiments, a heat capacity of wire 1301 is high enough to enable vaporization of craters having a depth of 20-100 μm.

In some embodiments, the wire is a metallic wire, for example made of tungsten, stainless steel, and/or copper. In some embodiments, wire 1301 is coated by a thin layer of glass or ceramics. In some embodiments, a diameter of wire 1301 ranges between 20-150 μm. A length of wire 1301 may range between 1-20 mm, depending on the type of application.

In some embodiments, one or more wires 1301, for example 4 wires as shown in this figure, are stretched between two plates 1303. Optionally, the wire is tightly stretched over the plates, for example to prevent it from deforming during operation.

In some embodiments, a plate 1303 is connected to a wheel 1305, for enabling rolling of the device over a surface of the tissue 1313.

In some embodiments, wire 1301 is attached, for example in opposite ends, to oppositely charged electrodes 1307. Optionally, electrodes 1307 are fixed in place with respect to wheels 1305. A current conductive structure such as brush-like structure 1309 having end points at point A and point B may be attached to each electrode. Electrodes 1307 are connected to a power source 1311, for example a battery.

During operation of the device, rotation of wheels 1305 causes the spinning of plates 1303. As wire 1301 contacts structure 1309, for example at point A, wire 1301 completes the electrical circuit, and current is conducted between electrodes 1307 through wire 1301. In some embodiments, point B is located close to the tissue 1313, for example less than 2 mm away from the tissue, and as wire 1301 advances through structure 1309 between points A and B (during the circular motion) it is heated, for example to 200-800 degrees Celsius, to vaporize the tissue. Optionally, once wire 1301 disengages point B, current is no longer conducted through wire 1301.

Optionally, wire 1301 cools as it rotates, for example until reaching point A again. A potential advantage of disconnecting wire 1301 includes limiting the amount of thermal energy that is delivered to the tissue.

In some embodiments, multiple wires used, and a distance between craters produced in the tissue is determined according to the number of wires and/or an advancing distance of the device, for example an advancing distance during a complete rotation of the wheels.

In some embodiments, the tissue is cooled after retraction of the wire 1301.

Optionally, cooling is performed by blowing air, for example as shown at 1315. Additionally or alternatively, cooling is performed by blowing a liquid mist, and/or by spraying liquid, and/or by placing a cold metallic plate on the tissue, and/or by a thermoelectric chiller.

In some embodiments, a motor is connected to the device. Optionally, the motor is configured for advancing the device at a certain velocity, for example a constant velocity of 1-20 cm/sec.

An exemplary device may include wheels and/or plates having a diameter of 1 cm, configured to roll a distance of ~3 cm during a single rotation (by having a circumference of ~3 cm). A plurality of wires, for example 5, 10, 15, 25, 30 wires or intermediate, larger or smaller number of wires, are stretched between the plates, for example with a 1 mm interval between them. A diameter of each wire is, for example, 50 μm. By rolling the device at a velocity of 10 cm/sec over the tissue, such as skin, a duration of contact of each wire with the skin is 500 μsec. Elongated, narrow craters, for example having a width of 50 μm, are formed every 1 mm in the tissue.

Optionally, a depth of the craters does not surpass the stratum corneum layer of the skin.

Parameters such as wire length and/or diameter and/or a number of wires and/or advancing distance and/or advancing velocity can be selected according to the type of application. For example, for treating scars, a wire length ranging between 1-10 mm is preferable. In some embodiments, different wires on a device have different lengths and/or widths, for producing a varied lesion pattern.

In some embodiments, at least a portion of the device, for example the wires, are detachable, and can be disposed of.

A Vaporizing Array for Nail Treatment

Figure 14:
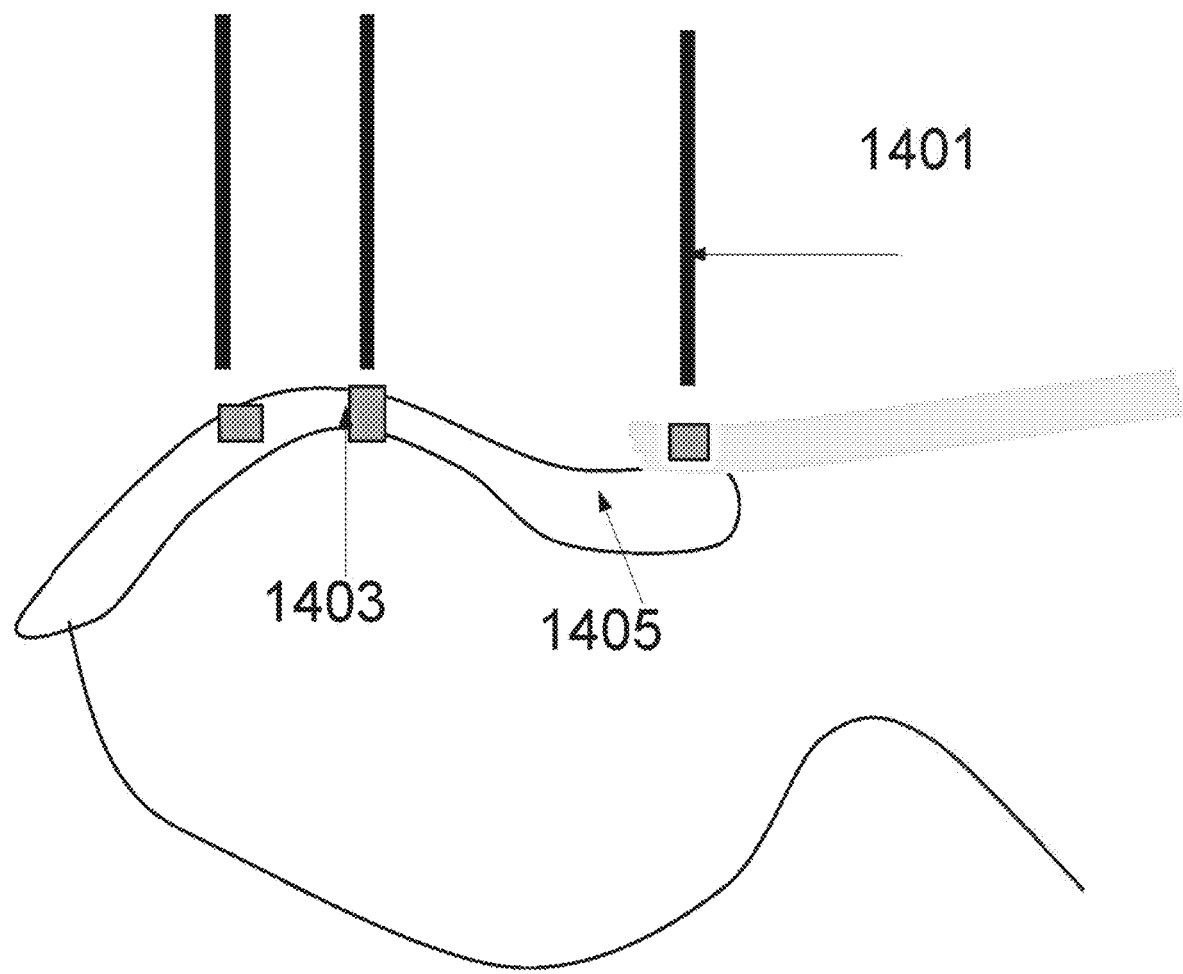
FIG. 14 illustrates the use of a vaporizing element, or an array of vaporizing elements, for penetrating through a nail, according to some embodiments of the invention.

FIG. 14 illustrates the use of a vaporizing element, or an array of vaporizing elements, for penetrating through a keratin layer of the nail, according to some embodiments of the invention.

Formation of craters through a keratin layer of the nail may be useful in treatment of onychomycosis, where liquid medication is applied to the nail to treat a fungal infection. As the keratin layer can be as thick as 100-300 μm, it may constitute a barrier which prevents the medication from penetrating the nail and attaining the surface of the infected underlying skin.

FIG. 14 illustrates vaporizing elements 1401 configured for vaporizing craters or holes 1403 through the nail 1405. In some embodiments, the vaporizing elements are shaped as cylindrical rods, pyramids, conical rods, or a combination thereof.

An optional treatment temperature profile used for vaporizing the keratin layer ranges, for example, between 400-500 degrees Celsius or higher. It is noted that fast heating of the elements may be significant, since a lower temperature, such as 170 degrees Celsius, will cause melting of the keratin layer as opposed to vaporization. If keratin is melted, it may become an additional barrier, interfering with the application of medication to the tissue underneath. In some embodiments, a treatment duration ranges between 1-100 msec.

The inventors have conducted an experiment where an array of pyramidal gold coated copper tips, having a base width of 1 mm, were heated to a temperature of 450 degrees Celsius and applied over a surface of a nail for a 100 msec duration. A crater having a depth of 300 μm was formed in the keratin layer.

In some embodiments, a single vaporizing element can be assembled in a pen-like housing, for example comprising a push-down button for a user to apply the element over the surface of the nail. Once one or more craters are formed, medication such as liquid medication can be applied, and pass through the formed craters to treat infected tissue.

A Vaporizing Array for Scar Treatment

Figure 15:
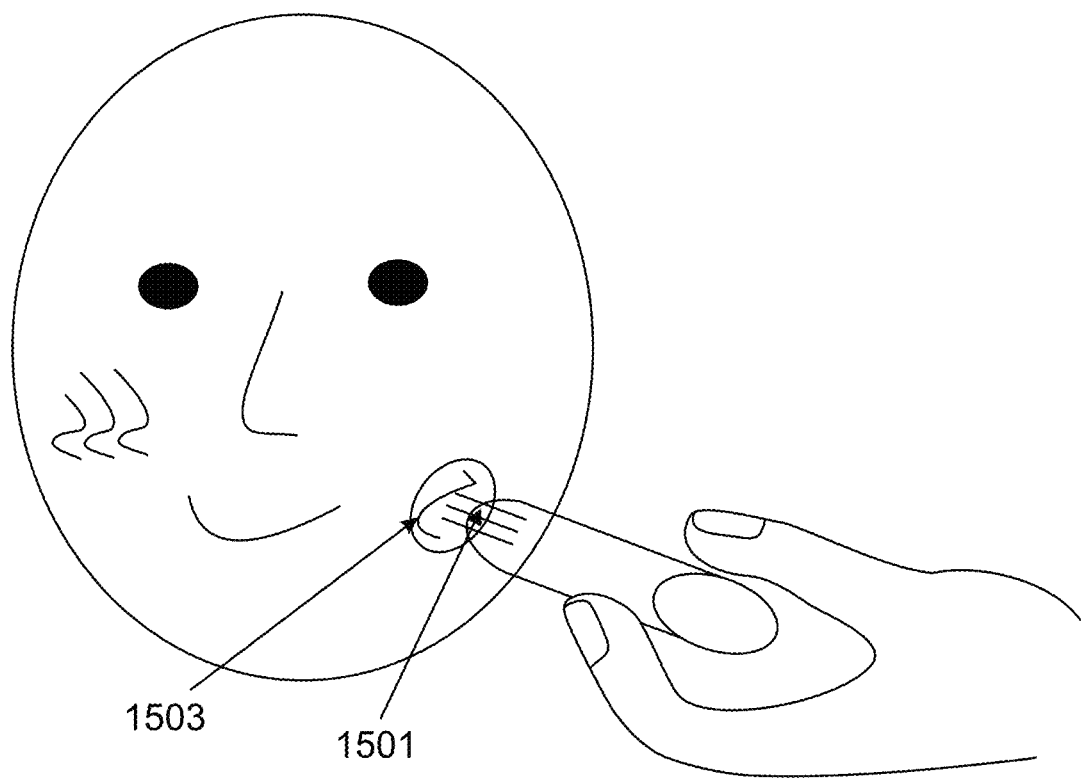
FIG. 15 illustrates the use of a vaporizing element, or an array of vaporizing elements, to treat scars in tissue, according to some embodiments of the inventions.

FIG. 15 illustrates the use of a vaporizing element or an array of vaporizing elements, to treat scars in tissue, according to some embodiments of the inventions.

In some embodiments, the vaporizing array 1501 is applied over scarred tissue 1503. In some embodiments, repetitive treatments are applied for gradually vaporizing the scar tissue, layer by layer. A time interval between repetitive treatments may range between 1 day- 2 months, depending on the type of tissue to be treated. In some embodiments, the time interval between treatments is determined such that a rate of formation of a new scar is smaller than the rate in which the old scar is vaporized, to prevent formation of a new scar.

In some embodiments, due the high temperature, such as 400 degrees Celsius, carbon particles which may reside on the walls of a vaporized crater are oxidized and transformed into $CO_2$ vapors, leaving the crater walls are char-free. Char-free crater walls may further promote healing of the tissue.

In some embodiments, the vaporizing elements used for scar treatment have a relatively flat and/or slightly rounded tip, to prevent unwanted penetration to a deeper layer of the scar tissue.

In some embodiments, a dwelling duration of the vaporizing elements in the tissue ranges between 10-100 msec.

In some embodiments, topical medication is applied to exposed scar tissue, for example applied before and/or after the treatment. It is noted that medication can be applied to any type of holes produced in the tissue, and not only to exposed tissue of scars. In some embodiments, medication comprises steroids, which may accelerate healing of the treated tissue such as scar tissue.

Figure 16A:
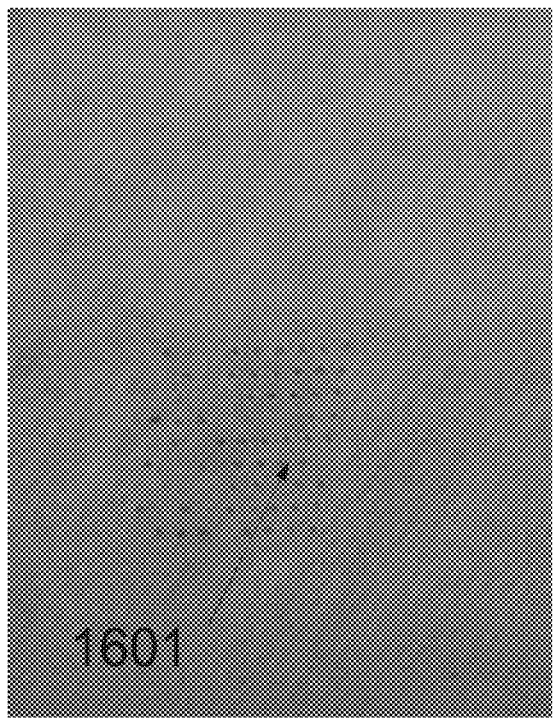
FIGS. 16A-B are photographs acquired 5 days following fractional skin resurfacing using vaporizing arrays made of different materials, according to some embodiments of the invention.
Figure 16B:
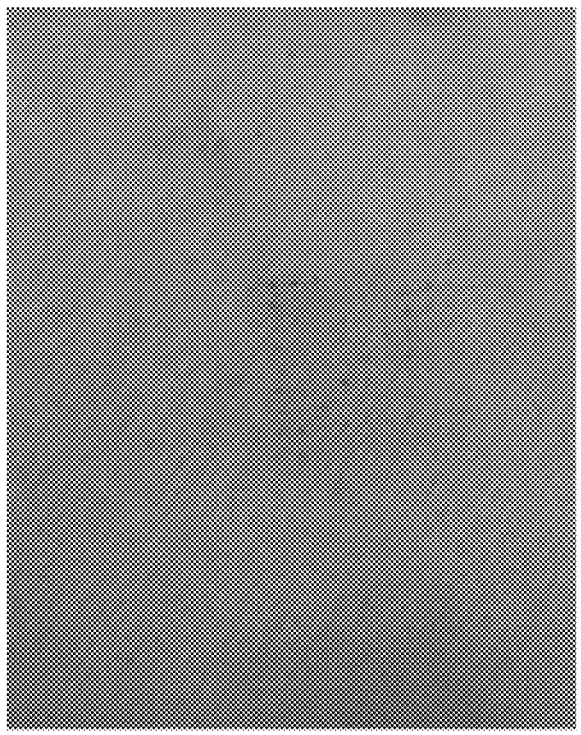

FIGS. 16A-B are photographs acquired 5 days following fractional skin resurfacing using vaporizing arrays made of different materials, according to some embodiments of the invention.

FIG. 16A shows arm skin treated with an array of pyramidal vaporizing elements made of stainless steel. FIG. 16B shows arm skin treated with an array of pyramidal vaporizing elements made of ALN.

The dimensions of a vaporizing element were a 1.25 mm base width, a 1.25 mm length (as measured from the plate to the distal end of the element), and a 200 μm width of the surface at a distal tip of the element. During treatment, both arrays were heated to a temperature ranging between 400-450° C.

The duration of contact with the tissue ranged between 14-25 msec for the stainless steel array, and 6-18 msec for the ALN array.

The darkened spots 1601 indicate locations of the formed craters, in which a crusting began to form during the healing. It is suggested that stainless steel elements can be used for achieving a mild treatment, while ALN can be used for a more aggressive treatment.

Exemplary Prism Shaped Vaporizing Element

Figure 17:
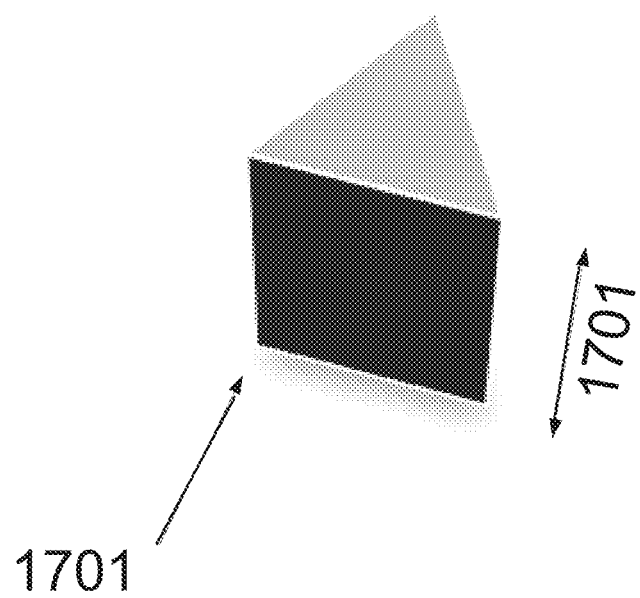
FIG. 17 shows an exemplary prism shaped vaporizing element, according to some embodiments of the invention.

FIG. 17 shows an exemplary prism shaped vaporizing tip 1701. In some embodiments, a length 1703 of the element ranges between 100 μm to 1 cm.

Optionally, an array of prism shaped elements comprises, for example, 10, 5, 15, 20, 30 or any other number of prism shaped element aligned in parallel to each other. Optionally, the array of prism shaped elements forms elongated craters in the tissue. A potential advantage includes relatively high compliance of the treated tissue to stretch in a perpendicular orientation with respect to the formed elongated craters, and may affect drug delivery to the tissue, as will be further elaborated. Additionally or alternatively, in some embodiments, a vaporizing element may take a parallelepiped form.

Figure 18:
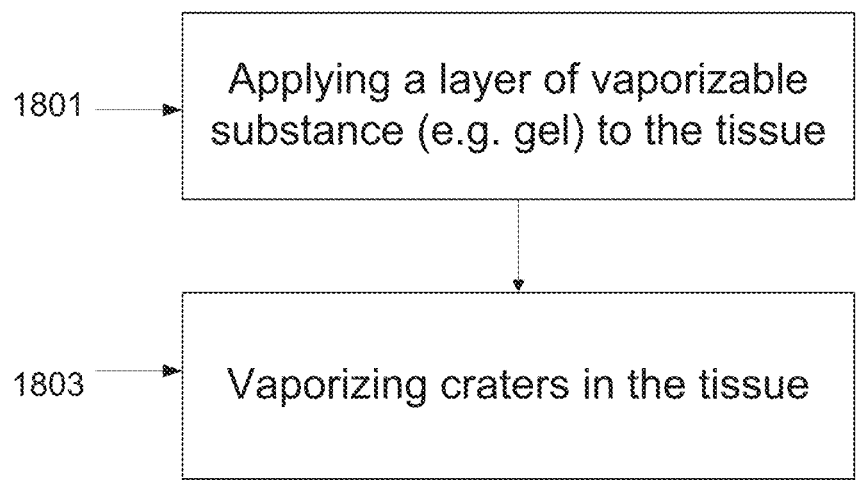
FIG. 18 is an exemplary method for vaporizing craters in tissue comprising the application of a vaporizable substance.

A Method for Vaporizing Tissue Comprising Application of a Vaporizable Substance to the Tissue FIG. 18 is an exemplary method for vaporizing tissue, such as skin, comprising the application of a vaporizable substance to the tissue prior to treating. In some embodiments, (1801), a layer of vaporizable substance such as water and/or gel, for example water based gel, is applied to the tissue. The water and/or gel may form a relatively homogenous surface on the tissue location intended for treatment, for example relative to the direct placing on skin tissue. Additionally or alternatively, the water and/or gel adhere to the surface of the tissue so that they match a topography of the surface. The vapors of water and/or gel are safe to the patient and medical personnel and thus these substances are suitable for use as vaporizable substances.

In some embodiments, the thickness of the vaporizable layer ranges between 10-80 μm, such as 20, 30, 50 μm. Craters can they be vaporized in the gel covered tissue (1803), for example using one or more vaporizing elements, optionally arranged in an array. Optionally, the applied substance is vaporized before the tissue is vaporized. One of the advantages of applying a substance such as water or gel may include controlling a depth of vaporization, optionally reducing the need of accurate control of movement of the vaporizing elements with respect to the tissue. For example, by applying a 30 μm thick layer of gel, and setting the vaporizing elements (e.g. using a control unit configured for activating the array) to vaporize a depth of 50 μm, 20 μm deep craters will be formed in the tissue. In some embodiments, application of gel is activated and/or controlled by the control unit. Optionally, the control unit is configured for determining a thickness of the gel.

An Exemplary Movement Profile Comprising Horizontal and Vertical Velocity Components FIGS. 19A-F show an exemplary movement profile of an array of vaporizing elements and/or a single vaporizing element, comprising a vertical velocity component v1, and a horizontal velocity component v2.

The movement profile generally described herein may be particularly useful in vaporization of the stratum corneum layer, which is the outermost layer of the epidermis. A potential advantage may include vaporizing the stratum corneum layer without damaging the epidermis layers underneath.

FIG. 19A shows an embodiment in which an array of vaporizing elements 1901, optionally configured at a distal end of a hand held vaporization device, is advanced towards the tissue (e.g. skin) 1903. In some embodiments, for example prior to contact with the tissue, the array is caused to slide in a horizontal direction, for example using a lever and/or motor and/or wheels, or other means suitable for advancing the array in parallel to the tissue. In some embodiments, by moving the array parallel to the tissue, a treated area may be shaped, for example, as a square (for example having an area of 200×200 µm^2, a size of 120×120 µm^2, a size of 400×400 µm^2 or intermediate, larger or smaller areas), a rectangle (for example having an area of 100×10,000 µm^2, 50×500 µm^2, 600×8000 µm^2, or intermediate, larger or smaller areas), or other shapes thereof. In some embodiments, the parallel movement is activated prior to contact with the tissue, for example when a distal tip of the vaporizing elements is only a small distance above the tissue, such as 0.7 mm, 0.5 mm, 0.2 mm above the tissue. Optionally, the horizontal movement is terminated once the vaporizing elements are lifted away from the tissue.

The embodiment shown at FIG. 19B includes a single vaporizing element, for example shaped as a rod 1905. Optionally, when no horizontal movement is applied (i.e. V2=0), a maximal penetration depth H of the element ranges between 50-100 µm, for example 60, 75, 90 µm or intermediate, larger or smaller depths. The treated surface area of the formed crater may be determined by a diameter D of rod 1905, for example ranging between 100-300 µm, such as 150, 20, 250 µm or intermediate, larger or smaller diameters. It is noted that D may represent not only a diameter but any width of the vaporizing element, for example if the element comprises a square or rectangular cross section profile.

FIG. 19C illustrates a movement pattern of a vaporizing rod 1905 for example as shown in FIG. 19B, comprising a horizontal velocity component.

Optionally, the horizontal velocity is constant. Alternatively, the horizontal velocity varies, for example increasing between a point of initial contact with tissue and a point of disengaging the tissue.

In some embodiments, the horizontal movement of rod 1905 forms a crater that smears across the tissue. Optionally, penetration depth H is reduced. For example, if the horizontal width of the formed crater is the diameter D multiplied by a factor N, for example ranging between 2-10 such as 3, 5, 7, or intermediate, larger or smaller values, the penetration depth H will optionally be reduced by the same factor N, arriving at a penetration depth of H/N.

In the following numerical example, diameter D=200 µm, penetration depth H (without applying horizontal velocity), 100 µm, and a duration of contact with the tissue=5 msec. Optionally, by applying a horizontal velocity of v2=40 cm/sec (200 µm/0.5 msec), a width of the formed crater increases during a contact time period of 5 msec to 2000 µm, for example instead of 200 µm which would have been formed if no horizontal velocity was applied. Since the dwelling time on an area of 200 µm is 5 msec, a factor of N=10 is obtained. Respectively, penetration depth H is reduced by N=10, arriving at 10 µm.

A potential advantage of moving a vaporizing element (or an array of vaporizing elements) horizontally may include increasing the precision of vaporization, for example, in the above described example, a device suitable for vaporizing craters having a depth of 100 µm is capable of vaporizing a depth of only 10 µm if an horizontal velocity component is added, thereby increasing the tolerance.

Optionally, such a device would be suitable for treating the stratum corneum without damaging deeper tissue layers, since a thickness of the stratum corneum of the skin is approximately 10 µm.

In some embodiments, a controller configured for operating the device is configured for selecting and/or modifying, automatically or by input received from a user, one or more parameters such as the penetration depth, a duration of contact with tissue, a vertical and/or horizontal velocity. Optionally, the controller is configured for selecting a size of the vaporizing element to be used. Optionally, the controller is configured for selecting and combining two or more parameters for affecting a third parameter, for example controlling the dwelling time of the element over a tissue location by selecting a horizontal velocity and and/or a size of the vaporizing element. In some embodiments, the controller is configured for applying treatment in pulses, for example for obtaining a deeper penetration depth is required (e.g. 20 µm instead of 10 µm).

The inventors have shown in experiments that in the treatment of skin, relatively small or no resistance of the tissue is encountered when moving the vaporizing element(s) horizontally across the skin. It is suggested that a sliding movement of the vaporizing element(s) across the skin is enabled, at least in part, by the elastic properties of the skin.

FIGS. 19D and 19E show an implementation of horizontal movement to a hand held device 1907. Device 1907 shown in FIG. 19D comprises a set of wheels 1909, configured to roll across the tissue. Optionally, the movement is motorized by a motor such as a DC or step motor. Optionally, the movement is controlled by a microprocessor. The device shown at FIG. 19E comprises a distal cup structure 1911 which is placed on the tissue. Optionally, vaporizing elements 1913 can pass through an opening 1915 or through designated holes in cup 1911. In some embodiments, a solenoid 1917 (or any spring or motor suitable for creating horizontal movement) is coupled to device 1907 to apply a horizontal force F for pushing the array across the tissue.

FIG. 19F provides an exemplary quantification calculation of the force F required for moving an array of vaporizing elements horizontally, for example for treating a stratum corneum layer of the skin. In an embodiment, force F is applied before contact is made between vaporizing elements 1913 and tissue 1919, as shown in the array position labeled A. Optionally, at position A, the horizontal velocity v2=0. After moving the array by a distance X, reaching position B, the velocity is increased to a maximal value v2=40 cm/sec. Optionally, the velocity remains constant during vaporization. If a weight of device 1907 is M, (for example M=500 gr), the horizontal acceleration of array 1913 will be F/M. A duration labeled t which is the time between position A and position B of the array fulfills the following equations:

$$X = a*t^2/2 \text{ and } v2 = a*t, \text{ therefore}$$

$$a = v2^2/(2x) \rightarrow F/M = v2^2/2x \rightarrow F = M*v2^2/2x$$

For values of M=500 gr, v2=40 cm/sec, X=4 mm, the required force F is equal $$F = (0.5 \times 16 \times 10^{-2})/(2 \times 4 \ 10^{-3}) \sim 10 \ N \sim 1 \ Kg \text{ force}.$$

In another example, wherein a single elongated vaporizing element in the form of a wire, for example having length of 1 cm and a diameter of 100 µm, the force F required for obtaining a horizontal velocity of 20 cm/sec for a handheld device weighing 100 gr, for a dwelling time of 500 µsec will be 70 gr force.

An Array Assembly Comprising One or More Piezoelectric Transducers

Figure 20:
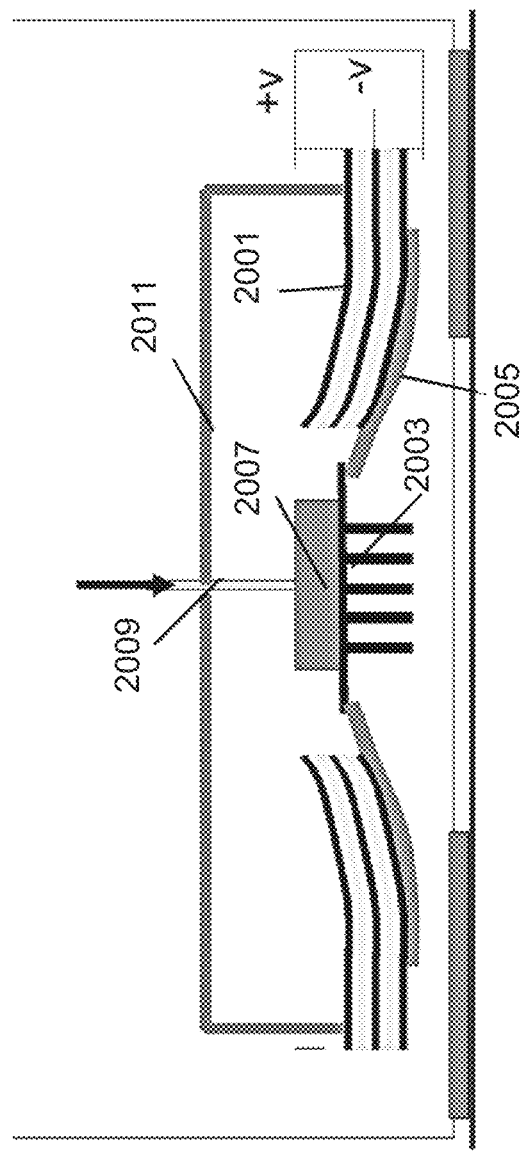
FIGS. 20A-B illustrate an array assembly comprising one or more piezoelectric transducers, according to some embodiments of the invention.
Figure 20:
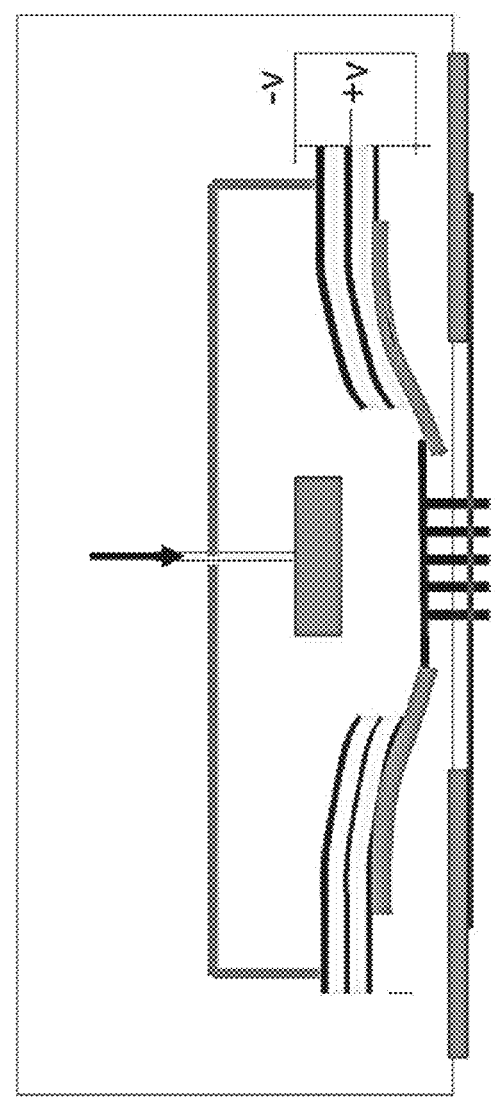

FIGS. 20A-B show an embodiment comprising one or more piezoelectric bimorph transducers 2001. In some embodiments, array 2003 is coupled to one or more thermally insulating rods 2005, which are also in contact with transducer 2001.

Optionally, by electrically activating transducer 2001, the transducer is deformed to bend towards heating element 2007, establishing electrical contact between the vaporizing elements of array 2003 and heating element 2007. Optionally, transducer 2001 is connected to a driving rod 2009, for example through frame 2011. In some embodiments, by driving rod 2009 in the distal and/or proximal directions (for example with the aid of a motor or spring, not shown in figure), heating element 2007 is raised or lowered simultaneously with the movement of piezoelectric transducers 2001.

In an embodiment, an assembly for example as described, comprising heating element 2007, piezoelectric transducers 2001, and array 2003 is lowered to a position in which the tips of array 2003 are in proximity to the tissue, yet not touching the tissue, for example the distal tips of the vaporizing elements of array 2003 are positioned 0.5 mm above a surface of the tissue. Optionally, at this point, as shown in FIG. 20A, array 2003 is in contact with heating element 2007, which heats the vaporizing elements to a temperature of, for example, 400 degrees Celsius. In some embodiments, a distance between the array and the tissue is identified by a controller.

Optionally, the controller is configured to activate the transducers based on the distance indication, for example by reversing a polarity of the applied potential. In some embodiments, as shown in FIG. 20B, the transducers deform in response to the applied voltage, de-coupling array 2003 from heating element 2007. Array 2003 is advanced in the distal direction so that the vaporizing elements penetrate through the tissue to vaporize it. A potential advantage of operating the array with the aid of piezoelectric transducers may include a short response time, enabling, for example, vaporization of the stratum corneum during 100 µsec or less, for example to a depth of 20 µm with an accuracy of approximately ±1 µm. Once the treating period is over, the controller may again reverse the polarity of the voltage applied to the transducer, re-establishing contact between array 2003 and heating element 2007.

In an exemplary embodiment, heating element 2007 and array 2003, while being coupled to each other, are moved to a distance of 250-500 µm above a surface of the skin, within a time period of, for example, 100 msec. The assembly is maintained at this position for a time period short enough so as to reduce or prevent damage to the skin due to infrared radiation from the heated vaporizing elements, for example 25 msec. In some embodiments, the piezoelectric transducer may comprise the following dimensions: a length L of 40 mm, a width W of 20 mm, and a thickness T of 0.5 mm. The deflection of the transducer is given by $2.7*10^{-3}*L^2$ meter/volt, namely 210 µm for 50 volt or 500 µm for 100 volt. The resonance frequency of the transducer is, for example, 150 Hz. Optionally, when activating the transducer at its resonant frequency, a single oscillation of the array is about 7 msec long. For an oscillation amplitude of 500 µm and oscillation time period of 7 msec, a dwelling duration of the array when reaching a penetration depth of 20 µm is less than 500 µsec. By varying the electrical potential for activating the transducer, the oscillation amplitude may be modified.

Additional Design of a Vaporizing Element Comprising a High Conductivity Core

Figure 21:
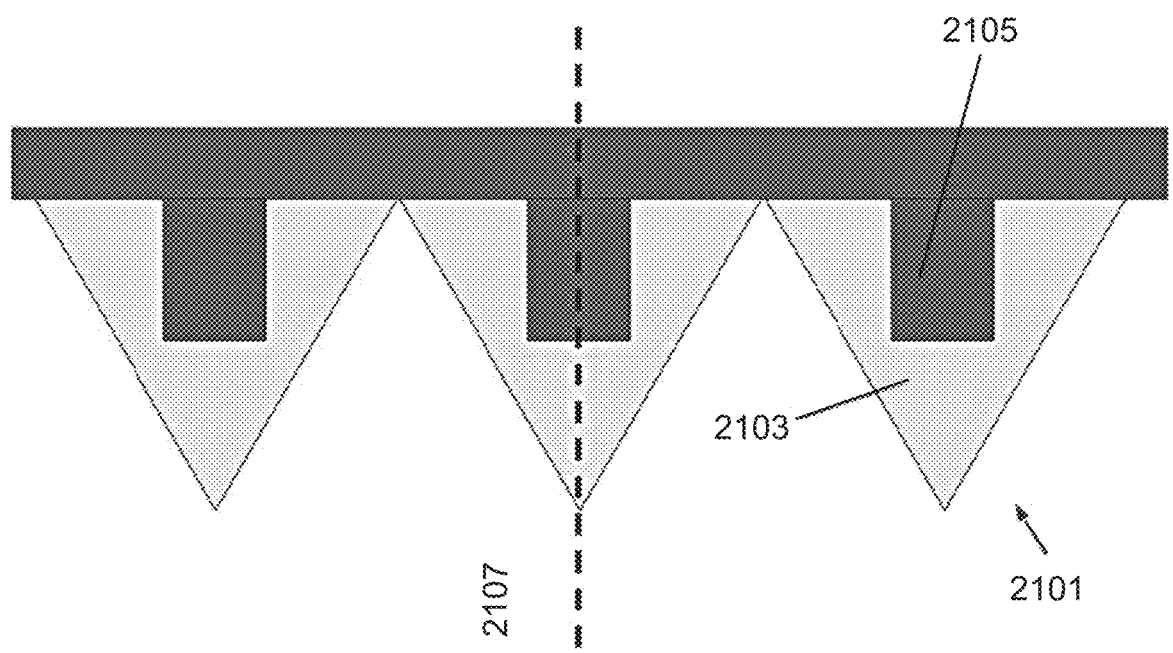
FIG. 21 shows a vaporizing element comprising a high conductivity core, according to some embodiments of the invention.

In some embodiments, as shown in FIG. 21 a vaporizing element 2101 is formed of a biocompatible material 2103, such as titanium or stainless steel, and a high conductivity core 2105, for example comprising copper. In some embodiments, core 2105 is shaped as a plug embedded within the element, for example a pyramidal element as shown in this figure. Optionally, the biocompatible layer 2103 is coated by a thin layer, for example less than 1 µm thick, of titanium oxide. Optionally, the titanium oxide layer is capable of withstanding high temperatures such as 700 degrees Celsius.

In some embodiments, a thermal relaxation time of the vaporizing element along axis 2107 (i.e. a time period required for returning to equilibrium) is reduced, if sufficient thermal contact is obtained between core 2105 and biocompatible layer 2103. For example, by incorporating (e.g. using a brazing process) a core 2105 having a length equal to a half of total length X of the vaporizing element, the thermal relaxation time may be reduced by approximately a factor of 4 (for example because the thermal relaxation time is proportional to $X^2$). Optionally, if core 2105 is formed of copper, having a heat conductivity of approximately 400 W/msec, and biocompatible layer 2103 is formed of stainless steel or titanium, having a thermal heat conductivity of 16-25 W/msec, an effective thermal conductivity of element 2101 is approximately 80 W/msec.

Figure 22:
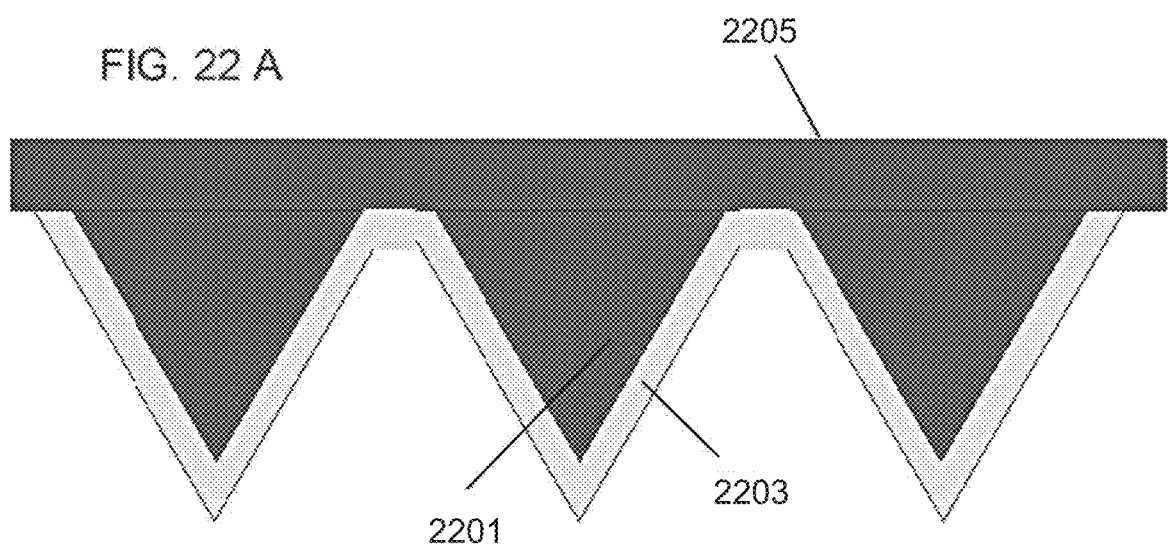
FIGS. 22A-B show a vaporizing element comprising a high conductivity core, according to some embodiments of the invention.
Figure 22:
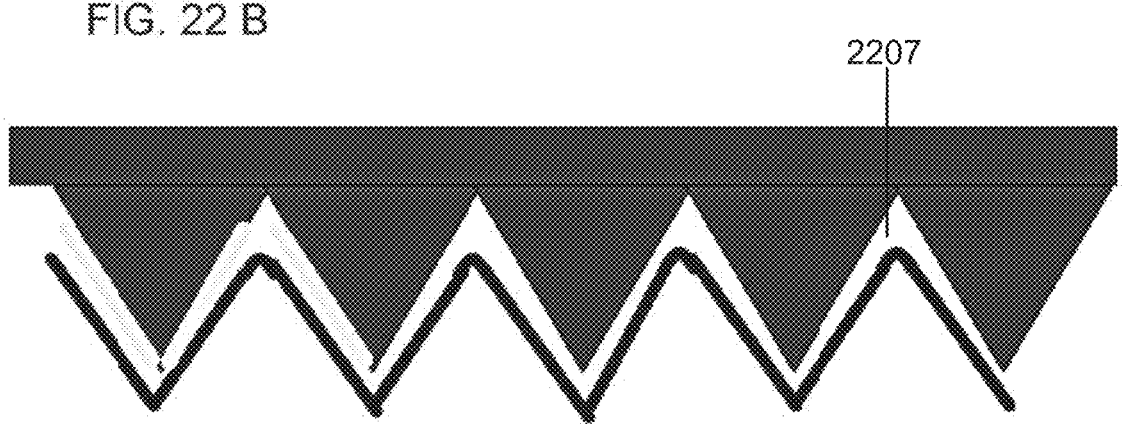

FIGS. 22A-B shows an embodiment in which core 2201 is formed of a material of high thermal conductivity, such as copper, coated by a thin biocompatible metallic sheet 2203, for example made of titanium and/or stainless steel. Optionally, sheet 2203 is manufactured according the shape of core 2201 of the vaporizing elements. Optionally, sheet 2203 comprises a constant thickness. Alternatively, sheet 2203 comprises a varying thickness. Optionally, sheet 2203 is sized to complete predetermined dimensions of the vaporizing element, for example having a thickness of 200 µm. In some embodiments, sheet 2203 is formed with a thickness of 10 µm, 50 µm, 150 µm, or intermediate, larger or smaller thicknesses. In some embodiments, sheet 2203 is produced using a coining process. Optionally, sheet 2203 is attached onto core 2201 by application of pressure. Optionally, sheet 2203 is brazed onto core 2201, for example brazed at a high temperature of 900 degrees Celsius, to enhance the contact between the materials for increasing the thermal conductivity, In some embodiments, craters of various depths are produced by vaporizing elements having different lengths and/or widths. Optionally, different lengths and/or widths of the elements are obtained by using a sheet 2203 that is formed with a varying thickness.

In some embodiments, for example as shown in FIG. 22B, sheet 2203 does not contact plate 2205 onto which the vaporizing elements are mounted. A potential advantage may include a simpler mounting process of sheet 2203 onto the cores 2201 of the vaporizing elements, which may the area of the sheet in contact with the core and enhance the coupling between them. Optionally, the mounting is performed by brazing, for example using an oven heated to approximately 900 degrees Celsius. It is possible that if air is trapped between the core and the sheet, it flows to space 2207 formed between the sheet and the plate.

It is expected that during the life of a patent maturing from this application many relevant vaporizing arrays and/or elements will be developed and the scope of the term vaporizing arrays and/or elements is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A device for vaporizing tissue, comprising:
an array of vaporizing elements mounted on a plate, said array of vaporizing elements formed of a first material of high thermal conductivity compared to titanium;
a first coating also having a high thermal conductivity compared to titanium coating said first material for maintaining said high thermal conductivity of said first material; and
a biocompatible titanium coating coating said first coating formed of a titanium compound, which remains biocompatible at a temperature of between 300-600 degrees Celsius,
wherein said biocompatible titanium coating reduces diffusion of said first material and said first coating when said array of vaporizing elements is heated to a temperature of at least 300 degrees Celsius;
wherein said first coating is selected from the group consisting of:
gold;
nickel; and
silver.

2. The device according to claim 1, wherein said array of vaporizing elements is a plurality of protruding tips.

3. The device according to claim 2, wherein a tip of at least a portion of said protruding tips is truncated.

4. The device according to claim 3, wherein said portion of said protruding tips with said truncated tip is shorter than at least one other protruding tip.

5. The device according to claim 2, wherein said plurality of protruding tips comprises a sharp distal tip.

6. The device according to claim 2, wherein said plurality of protruding tips have a spatial distribution ranging between 2 and 100 protruding tips per square centimeter.

7. The device according to claim 2, wherein said plurality of protruding tips are in a shape selected from a group consisting of:
a pyramidal shape; and
a conical shape.

8. The device according to claim 2, wherein said plate has a heat capacity selected so as to produce a hole in a tissue layer having a depth smaller than 20 μm.

9. The device according to claim 2, wherein said plurality of protruding tips comprises a blunt distal tip.

10. The device according to claim 1, wherein one or more of said first material, said titanium compound, and an additional material coating said titanium compound reduce IR emissivity towards the tissue.

11. The device according to claim 1, wherein said plate is planar and has surface area ranging between 0.0001 $cm^2$-1 $cm^2$.

12. The device according to claim 1, wherein said plate is formed of copper.

13. The device according to claim 1, wherein said biocompatible titanium coating is formed as a sheet having a thickness less than 500 μm.

14. The device according to claim 1, wherein said biocompatible titanium coating is formed with varying thickness.

15. The device according to claim 1, wherein said first material selected from a group consisting of:
- a sintered material; and
- a coined material.

16. The device according to claim 1, further comprising a space between said plate and said biocompatible coating.

17. The device according to claim 1, wherein said biocompatible coating does not contact said plate.

18. The device according to claim 1, wherein said titanium compound is selected from the group consisting of:
- titanium;
- titanium nitride; and
- titanium oxide.

19. The device according to claim 1, wherein said first material is selected from the group consisting of:
- copper; and
- aluminum nitride (ALN).

20. The device according to claim 1, further comprising:
- a heating element, coupled with said array of vaporizing elements, for heating said array of vaporizing elements to said temperature of at least 300 degrees Celsius; and
- a power source, coupled with said heating element, for supplying power to said heating element.

21. A device for vaporizing tissue, comprising:
- an array of vaporizing elements mounted on a plate, said array of vaporizing elements formed of a first material of high thermal conductivity compared to titanium;
- a first coating also having a high thermal conductivity compared to titanium coating said first material for maintaining said high thermal conductivity of said first material; and
- a biocompatible titanium coating coating said first coating formed of a titanium compound, which remains biocompatible at a temperature of between 300-600 degrees Celsius,
- wherein said biocompatible titanium coating reduces diffusion of said first material and said first coating when said array of vaporizing elements is heated to a temperature of at least 300 degrees Celsius;
- wherein said first material is selected from the group consisting of:
  - copper; and
  - aluminum nitride (ALN); and
- wherein said first coating is selected from the group consisting of:
  - gold;
  - nickel; and
  - silver.

22. A device for vaporizing tissue, comprising:
- an array of vaporizing elements mounted on a plate, said array of vaporizing elements formed of a first material of high thermal conductivity compared to titanium;
- a first coating coating said first material for maintaining said high thermal conductivity;
- a biocompatible titanium coating coating said first coating formed of a titanium compound, which remains biocompatible at a temperature of between 300-600 degrees Celsius; and
- a second coating coating said biocompatible titanium coating, for providing mechanical protection to said array of vaporizing elements,
- wherein said biocompatible titanium coating reduces diffusion of said first material and said first coating when said array of vaporizing elements is heated to a temperature of at least 300 degrees Celsius.

23. The device according to claim 22, wherein said second coating is selected from the group consisting of:
- ceramic;
- glass; and
- titanium oxide.

24. The device according to claim 22, wherein said second coating is also for withstanding high operating temperatures, above 400 degrees Celsius, of said device.

* * * * *